US 12,390,639 B2

(12) United States Patent
Crosson

(10) Patent No.: US 12,390,639 B2
(45) Date of Patent: Aug. 19, 2025

(54) SYSTEMS AND METHOD FOR DELIVERING PULSED ELECTRIC CURRENT TO LIVING TISSUE

(71) Applicant: TrueRelief, LLC, Santa Monica, CA (US)

(72) Inventor: John Crosson, Santa Monica, CA (US)

(73) Assignee: TRUERELIEF, LLC, Santa Monica, CA (US)

( * ) Notice: Subject to any disclaimer, the term of this patent is extended or adjusted under 35 U.S.C. 154(b) by 0 days.

(21) Appl. No.: 18/140,297

(22) Filed: Apr. 27, 2023

(65) Prior Publication Data

US 2023/0256245 A1    Aug. 17, 2023

Related U.S. Application Data

(63) Continuation of application No. 17/538,379, filed on Nov. 30, 2021, now Pat. No. 11,666,758, which is a
(Continued)

(51) Int. Cl.
*A61N 1/36*    (2006.01)
*A61N 1/04*    (2006.01)

(52) U.S. Cl.
CPC ..... *A61N 1/36021* (2013.01); *A61N 1/36034* (2017.08); *A61N 1/0456* (2013.01)

(58) Field of Classification Search
USPC .......................................................... 607/46
See application file for complete search history.

(56) References Cited

U.S. PATENT DOCUMENTS

| 945,564 A | 1/1910 | Marko |
|---|---|---|
| 4,014,346 A | 3/1977 | Brownlee |

(Continued)

FOREIGN PATENT DOCUMENTS

| AU | 2020200898 A1 | 2/2020 |
|---|---|---|
| CA | 2774272 A1 | 3/2010 |

(Continued)

OTHER PUBLICATIONS

International Search Report and Written Opinion in International Application No. PCT/US2011/061451, mailed Jul. 25, 2012 (10 pages).

(Continued)

*Primary Examiner* — Ahmed M Farah
(74) *Attorney, Agent, or Firm* — ICE MILLER LLP; Justin D. Swindells

(57) ABSTRACT

A patient treatment unit for delivering non-invasive pulsed energy to living tissue with a probe stimulus generator circuit configured to output, as a treatment signal, a sequence of DC electrical pulses at a controlled pulse frequency of about 20 kHz and having a pulse voltage defined by a variable supply voltage of the probe stimulus generator circuit. The unit includes primary and secondary probes for contacting a body, an intensity adjustment circuit configured to control the variable supply voltage, and an electronic timer display configured to display an elapsed time in decimal numbers in minute and second format. An electrical current of the pulses is in a range of 0.1-2 mA while the probes are contacting the body. An operating output voltage across the probes while conducting the treatment signal does not exceed a maximum operating output voltage of 165 VDC while the probes are contacting the body.

22 Claims, 8 Drawing Sheets

Related U.S. Application Data continuation of application No. 17/033,099, filed on Sep. 25, 2020, now Pat. No. 11,197,999, which is a continuation of application No. PCT/US2020/037625, filed on Jun. 12, 2020.

(60) Provisional application No. 62/860,678, filed on Jun. 12, 2019.

(56) References Cited

U.S. PATENT DOCUMENTS

| | | |
|---|---|---|
| 4,014,347 A | 3/1977 | Halleck |
| 4,112,923 A | 9/1978 | Tomecek |
| 4,173,741 A | 11/1979 | Kameny |
| 4,315,503 A | 2/1982 | Ryaby |
| 4,319,584 A | 3/1982 | McCall |
| 4,376,901 A | 3/1983 | Pettibone |
| 4,455,527 A | 6/1984 | Singer |
| 4,714,886 A | 12/1987 | Halpern |
| 4,769,881 A | 9/1988 | Pedigo |
| 4,926,865 A | 5/1990 | Oman |
| 4,977,895 A | 12/1990 | Tannenbaum |
| 5,045,988 A | 9/1991 | Gritter |
| 5,109,847 A | 5/1992 | Liss |
| 5,231,354 A | 7/1993 | Leunbach |
| 5,304,211 A | 4/1994 | Israel |
| 5,343,869 A | 9/1994 | Pross |
| 5,347,221 A | 9/1994 | Rubinson |
| 5,505,932 A | 4/1996 | Grinstaff |
| 5,517,119 A | 5/1996 | Weinstock |
| 5,571,149 A | 11/1996 | Liss |
| 5,573,552 A | 11/1996 | Hansjurgens |
| 5,584,863 A | 12/1996 | Rauch |
| 5,592,086 A | 1/1997 | Weinstock |
| 5,645,526 A | 7/1997 | Flower |
| 5,674,261 A | 10/1997 | Smith |
| 5,723,001 A | 3/1998 | Pilla |
| 5,814,078 A | 9/1998 | Zhou |
| 5,865,746 A | 2/1999 | Murugesan |
| 5,900,227 A | 5/1999 | Janzen |
| 5,945,564 A | 8/1999 | Takayanagi |
| 6,110,106 A | 8/2000 | MacKinnon |
| 6,140,346 A | 10/2000 | Andrulis |
| 6,157,854 A | 12/2000 | Haber |
| 6,238,425 B1 | 5/2001 | Thiberg |
| 6,242,919 B1 | 6/2001 | Zuk |
| 6,302,900 B1 | 10/2001 | Riggs |
| 6,319,682 B1 | 11/2001 | Hochman |
| 6,335,625 B1 | 1/2002 | Bryant |
| 6,430,430 B1 | 8/2002 | Gosche |
| 6,461,375 B1 | 10/2002 | Baudry |
| 6,465,507 B2 | 10/2002 | Tang |
| 6,495,601 B1 | 12/2002 | Hochman |
| 6,496,725 B2 | 12/2002 | Kamada |
| 6,566,874 B1 | 5/2003 | Speier |
| 6,573,063 B2 | 6/2003 | Hochman |
| 6,594,527 B2 | 7/2003 | Mo |
| 6,633,779 B1 | 10/2003 | Schuler |
| 6,671,540 B1 | 12/2003 | Hochman |
| 6,689,806 B1 | 2/2004 | Tang |
| 6,706,709 B2 | 3/2004 | Tang |
| 6,751,506 B2 | 6/2004 | Shealy |
| 6,766,202 B2 | 7/2004 | Underwood |
| 6,775,573 B2 | 8/2004 | Schuler |
| 6,776,573 B2 | 8/2004 | Arilla |
| 6,836,114 B2 | 12/2004 | Reddy |
| 6,845,262 B2 | 1/2005 | Albert |
| 6,974,415 B2 | 12/2005 | Cerwin |
| 7,002,147 B1 | 2/2006 | Hansknecht |
| 7,010,356 B2 | 3/2006 | Jog |
| 7,058,446 B2 | 6/2006 | Schuler |
| 7,082,325 B2 | 7/2006 | Hashimshony |
| 7,092,760 B2 | 8/2006 | Foster |
| 7,117,034 B2 | 10/2006 | Kronberg |
| 7,150,710 B2 | 12/2006 | Haber |
| 7,158,004 B2 | 1/2007 | Ahn |
| 7,174,213 B2 | 2/2007 | Pless |
| 7,198,776 B2 | 4/2007 | Klaveness |
| 7,483,734 B2 | 1/2009 | Colthurst |
| 7,574,257 B2 | 8/2009 | Rittman |
| 7,603,171 B2 | 10/2009 | Eror |
| 7,613,517 B2 | 11/2009 | Goroszeniuk |
| 7,801,585 B1 | 9/2010 | Weinstock |
| 7,847,644 B2 | 12/2010 | Suzuki |
| 8,064,988 B2 | 11/2011 | Weinstock |
| 8,108,047 B2 | 1/2012 | Schumann |
| 8,326,398 B2 | 12/2012 | Weinstock |
| 8,849,371 B2 | 9/2014 | Weinstock |
| 9,079,029 B2 | 7/2015 | Weinstock |
| 9,149,386 B2 | 10/2015 | Fahey |
| 9,238,138 B2 | 1/2016 | Lee |
| 9,308,363 B2 | 4/2016 | Goroszeniuk |
| 9,550,068 B2 | 1/2017 | Weinstock |
| 9,737,709 B2 | 8/2017 | Bachinski |
| 10,130,805 B2 | 11/2018 | Schonenberger |
| 10,499,848 B2 | 12/2019 | Weinstock |
| 10,960,207 B2 | 3/2021 | Wong |
| 11,197,999 B2 * | 12/2021 | Crosson ............. A61N 1/36021 |
| 11,198,000 B2 * | 12/2021 | Crosson ............. A61N 1/36021 |
| 11,666,758 B2 * | 6/2023 | Crosson ............. A61N 1/36021 |
| | | 607/46 |
| 2001/0039375 A1 | 11/2001 | Lee |
| 2002/0042427 A1 | 4/2002 | Tang |
| 2002/0052369 A1 | 5/2002 | Tang |
| 2002/0055092 A1 | 5/2002 | Hochman |
| 2003/0083724 A1 | 5/2003 | Jog |
| 2003/0130709 A1 | 7/2003 | D.C. |
| 2004/0015188 A1 | 1/2004 | Coulter |
| 2005/0027333 A1 | 2/2005 | Lennox |
| 2005/0033381 A1 | 2/2005 | Carter |
| 2005/0158285 A1 | 7/2005 | Giampapa |
| 2005/0165459 A1 | 7/2005 | Coulter |
| 2005/0177201 A1 | 8/2005 | Freeman |
| 2005/0177202 A1 | 8/2005 | Classen |
| 2005/0197555 A1 | 9/2005 | Mouradian |
| 2006/0052720 A1 | 3/2006 | Ross |
| 2007/0060800 A1 | 3/2007 | Drinan |
| 2007/0106342 A1 | 5/2007 | Schumann |
| 2007/0129759 A1 | 6/2007 | Colthurst |
| 2007/0179585 A1 | 8/2007 | Moretti |
| 2008/0109049 A1 | 5/2008 | Schumann |
| 2008/0183098 A1 | 7/2008 | Denison |
| 2009/0149732 A1 | 6/2009 | Weinstock |
| 2009/0270952 A1 | 10/2009 | Weinstock |
| 2010/0204752 A1 | 8/2010 | Tremblay |
| 2010/0324627 A1 | 12/2010 | Weinstock |
| 2011/0166622 A1 | 7/2011 | Crosson |
| 2011/0301450 A1 | 12/2011 | Hue |
| 2013/0172838 A1 | 7/2013 | Tremblay |
| 2017/0361095 A1 | 12/2017 | Mueller |
| 2019/0008410 A1 | 1/2019 | Crosson |
| 2019/0388278 A1 | 12/2019 | Donda |
| 2020/0077943 A1 | 3/2020 | Weinstock |
| 2021/0008369 A1 | 1/2021 | Crosson |
| 2022/0080196 A1 | 3/2022 | Crosson |

FOREIGN PATENT DOCUMENTS

| | | |
|---|---|---|
| DE | 2 443 913 A1 | 4/1976 |
| DE | 2443913 | 4/1976 |
| EP | 0 662 311 A1 | 7/1995 |
| EP | 0662311 | 7/1995 |
| EP | 1 537 893 A2 | 6/2005 |
| EP | 1537893 | 6/2005 |
| GB | 02434544 A | 8/2007 |
| JP | H 10-509600 A | 9/1998 |
| JP | 2003-062034 A | 7/2001 |
| JP | 2001-187035 A | 3/2003 |
| JP | 2004-243047 A | 9/2004 |
| JP | 2008-125694 | 6/2008 |
| JP | 2010-534114 A | 11/2010 |
| JP | 2013-544177 | 12/2013 |
| WO | WO 96/10440 A1 | 4/1996 |
| WO | WO 03/076009 A1 | 9/2003 |

(56) References Cited

FOREIGN PATENT DOCUMENTS

| WO | WO 2005/118061 A1 | 12/2005 |
|---|---|---|
| WO | WO 2007/075410 A2 | 7/2007 |
| WO | WO 2007/088348 A2 | 8/2007 |
| WO | WO 2010/031055 A1 | 3/2010 |
| WO | WO 2011/106225 A2 | 9/2011 |
| WO | WO 2017/156340 A1 | 9/2017 |
| WO | WO 2020/252406 A1 | 12/2020 |

OTHER PUBLICATIONS

Notice of Allowance corresponding to Japanese Patent Application No. 2013-542044, Japanese Patent Office, dated May 17, 2016 (2 pages).

Peeters, A.M.G., "Single-Rail Handshake Circuits," Dissertation published by Proefschrift Technische Universiteit Eindhoven, 1996. ISBN 90-74445-28-4 (202 pages).

Engstrom, S., "Resonances and Magnetic Field Detection in Biological Systems," Electricity and Magnetism in Biology and Medicine, pp. 223-226; 1999 (4 pages).

Muehsam, D.J. & Pilla, A.A., "The Sensitivity of Cells and Tissues to Exogenous Fields: Dependence Upon Target System Initial State," Electricity and Magnetism in Biology and Medicine, pp. 405-408; 1999 (4 pages).

Pilla, A.A. et al., "A Larmor Precession/Dynamical System Model Allows uT-Range Magnetic Field Effects on Ion Binding in the Presences of Thermal Noise," Electricity and Magnetism in Biology and Medicine, pp. 395-399; 1999 (5 pages).

Yasui, M. et al., "Effect of Magnetic Field Exposure on Calcium Channel Currents Using Patch-Clamp Technique," Electricity and Magnetism in Biology and Medicine, pp. 581-584; 1999 (4 pages).

International Search Report and Written Opinion in International Application No. PCT/US2006/043582, mailed Mar. 26, 2007 (13 pages).

International Search Report and Written Opinion in International Application No. PCT/US2009/056990, mailed Nov. 2, 2009 (7 pages).

International Search Report and Written Opinion in International Application No. PCT/US2011/025162, mailed Oct. 31, 2011 (7 pages).

International Search Report and Written Opinion in International Application No. PCT/US2020/037625, mailed Oct. 6, 2020 (14 pages).

* cited by examiner

SYSTEMS AND METHOD FOR DELIVERING PULSED ELECTRIC CURRENT TO LIVING TISSUE

CROSS-REFERENCE TO RELATED APPLICATIONS

This application is a continuation of U.S. application Ser. No. 17/538,379, filed Nov. 30, 2021, now allowed, which is a continuation of U.S. application Ser. No. 17/033,099, filed Sep. 25, 2020, now U.S. Pat. No. 11,197,999, which is a continuation of International Application No. PCT/US20/37625, filed Jun. 12, 2020, which claims priority under 35 U.S.C. § 119 to and the benefit of U.S. Provisional Patent Application Ser. No. 62/860,678, filed on Jun. 12, 2019, and titled "System And Method For Delivering Pulsed Electric Current To Living Tissue," all which is incorporated herein by reference in their entireties.

FIELD OF THE INVENTION

The present invention relates generally to a device unit and methods for treatment of pain, and, more particularly, to delivering pulsed electrical or electromagnetic energy in a non-invasive, patient-specific manner.

BACKGROUND OF THE INVENTION

Over the past 12 years, probably over 10,000 patient treatments have been given with treatment units for relieving pain. These treatments include a diverse range of patients—young, old, and in-between, as well as both male and female. The patients had various states of health, from the extremely physical fit (e.g., professional athletes) to the out of shape and infirmed. The patients typically have a very wide range of preexisting conditions, including sports and other acute injuries, long-standing chronic issues that in some cases have lasted 15+ years, and symptoms that are common byproducts of just completed surgery.

The initial goal of these treatments and associated technology has been to reduce or eliminate people's pain, which has been accomplished to a degree. However, one problem associated with these previous treatments is that they have a cumulative effect and take many treatments, sometimes of long durations, to achieve some form of enduring pain relief. Often it would take as many as 15-20 treatments over many weeks, and individual treatments could take thirty minutes or more. Because durable outcomes require many treatments and a significant time commitment from the patient, the number of treatments and the time period involved (3-5 weeks) is an impediment to the patient's commitment to continue to come for treatments, which in turn is a great inhibitor to great, enduring outcomes.

Yet another problem with current treatment units is that they do not display elapsed treatment time for session time in a specific treatment location that is resettable for each treatment location or in a form that is understandable by laypeople. Without a meaningful timer that shows these times in a layperson-understandable form, there is a high potential for under treatment, which greatly diminishes patient outcomes.

Yet another problem with current treatments is that the wide ranging options for adjusting the frequency of the treatment current and the almost unlimited ways the treatment provider can place the treatment probes on the patient's body create endless permutations and combinations of treatments, many or most of which being sub-optimal and leading to less-efficacious outcomes. Further, these sub-optimal treatment choices made by the treatment provider can often create only transient pain relief, rather than healing for the underlying condition and/or long-term pain relief. With approximately 24% of patients having no meaningful pain relief, the opportunity for more carefully considered or precise therapy, both in terms of electrical composition and probe placement, is to reduce the numbers of patients for whom the therapy has not worked.

Thus, there is a great need for providing a treatment unit and associated method that is more precise in optimizing the opportunity offered by the technology to not only provide enduring pain relief but to also heal and/or to prevent or reduce the above and other problems.

SUMMARY OF THE INVENTION

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter. This summary is also not intended to be used in isolation to determine the scope of the claimed subject matter. The subject matter should be understood by reference to appropriate portions of the entire specification of this disclosure, any or all drawings and each claim.

According to an embodiment of the present disclosure, a method is disclosed of treating pain or inflammation or a wound in a patient to reduce or treat the pain or inflammation or wound. The method includes the steps of: initiating a first treatment cycle using a patient treatment unit, the first treatment cycle including: placing a first conductor and a second conductor at first and second locations onto living tissue of a body of a human or animal in an area where pain or inflammation or wound is indicated, the first conductor having an electrically conductive tip, the first and second conductors being electrically coupled to the patient treatment unit having a first timer display configured to display a resettable timer, applying firm pressure to at least the first conductor while the tip contacts the living tissue, causing electrical energy to be delivered through the first and second conductors and into the tissue in the form of a treatment signal supplied by the patient treatment unit, the treatment signal including a pulse train of direct current (DC) pulses having a pulse frequency in a range between 18 and 22 kiloHertz (kHz), a pulse current from 0.1 milliAmperes (mA) to 6.0 mA, and a pulse voltage dependent on a variable supply voltage supplied to the probe stimulus generator circuit and providing a maximum pulse voltage of about 165 Volts of DC (VDC).

The method further includes, during the first treatment cycle, monitoring an elapsed time of the first treatment cycle on the timer that starts from the initiating the first treatment cycle and ends upon cessation of delivery of the electrical energy to end the first treatment cycle; terminating the first treatment cycle and stopping the timer; initiating a second treatment cycle, which includes: keeping or placing the first conductor at the first location or a new location onto the body while applying firm pressure to at least one of the first conductor or the second conductor, causing the electrical energy to be delivered through the body, and holding the first conductor stationary during at least part of the second treatment cycle or moving the first conductor along the body during at least part of the second treatment cycle while maintaining firm pressure on the first conductor, and monitoring an elapsed time of the second treatment cycle on the timer that restarts upon the initiating the second treatment cycle. The method includes terminating the second treatment cycle.

The first treatment cycle lasts 2-5 minutes, and the second treatment cycle has the same or a different duration relative to the first treatment cycle. The second treatment cycle lasts a shorter duration relative to the first treatment cycle. The first treatment cycle further includes monitoring an impedance or conductivity of the body and responsive to observing no change therein during the first treatment cycle, maintaining the first conductor at the same location in the second treatment cycle. The first treatment cycle includes moving the first conductor during at least part of the first treatment cycle. The first treatment cycle includes moving the second conductor during at least part of the first treatment cycle towards or away from the first conductor.

The same firm pressure is applied to the first conductor and to the second conductor during at least one of the first treatment cycle or the second treatment cycle. The firm pressure includes an applied weight of 0.05 to 10 pounds. The timer is displayed in decimal minutes and seconds format.

The terminating the first treatment cycle is carried out by picking up at least one of the first conductor or the second conductor from the body to interrupt the delivery of the electrical energy through the body or by selecting a switch on the first conductor or on the second conductor or on the patient treatment unit to stop the delivery of the electrical energy regardless of whether the first and second conductors are touching the body.

The placing the first conductor includes placing the first conductor at an approximately orthogonal orientation relative to a surface of the body. The surface of the body corresponds to a finger, a knee, a shoulder, a hip, a joint, or a nerve on the body. The placing the first conductor includes placing the first conductor at approximately a 45 degree angle relative to a muscle on the body.

The first treatment cycle includes moving the first conductor during at least part of the first treatment cycle, the moving the first conductor including moving the first conductor around the muscle to treat a muscle trigger point on the body while maintaining the first conductor at approximate the 45 degree angle relative to the body. The first treatment cycle includes moving the first conductor during at least part of the first treatment cycle, wherein the electrically conductive tip is rounded and has a diameter of ¼ inches. The second conductor includes an electrically conductive tip that is rounded and has a diameter of ¼ inches.

The method can further include repeating the first treatment cycle or the second treatment cycle one or more times to accumulate a total elapsed treatment time, the total elapsed treatment time not exceeding 10 minutes and the first treatment cycle or the second treatment cycle does not exceed 4 minutes.

A total elapsed treatment time does not exceed 8 minutes. The methods herein can be used to treat pain, or inflammation, or a wound in the human or animal. The wound can include a diabetic wound, an ulcer, an infection, a cut, or an incision wound.

According to another embodiment of the present disclosure, a method of treating pain or inflammation or a wound in a patient to reduce or eliminate the pain or inflammation or wound is disclosed. The method includes: initiating a treatment cycle by placing a first conductor and a second conductor onto living tissue of a body of a human or animal in an area where pain or inflammation or wound is indicated, the first conductor having a rounded tip that is electrically conductive, the first and second conductors being electrically coupled to a patient treatment unit having a first timer display configured to display a resettable running timer; applying firm pressure to at least the first conductor while the rounded tip is pressed against the living tissue; causing electrical energy to be delivered through the first and second conductors and into the tissue in the form of a treatment signal supplied by the patient treatment unit, the treatment signal including a pulse train of direct current (DC) pulses having a pulse frequency in a range between 18 and 22 kiloHertz (kHz), a pulse current from 0.1 milliAmperes (mA) to 6 mA, and a pulse voltage dependent on a variable supply voltage supplied to the probe stimulus generator circuit, the variable supply voltage providing a maximum pulse voltage of about 165 Volts of DC (VDC).

The method includes, while maintaining the firm pressure on the first conductor as the electrical energy is supplied through the body, moving at least the first conductor along the body in a direction along which a pain signal traverses the body and monitoring an elapsed time of treatment on the running timer starting from a start of the delivery of the electrical energy through the conductors; responsive to the elapsed time lasting a first duration, stopping the timer and picking up the at least first conductor and placing at least the first conductor at the same or a new location on the body and applying the firm pressure there; and resetting the timer.

The placing the first conductor includes placing the first conductor at an approximately orthogonal orientation relative to a surface of the body. The surface of the body corresponds to a finger, a knee, a shoulder, a hip, a joint, or a nerve on the body. The second conductor has a rounded tip that is electrically conductive and is held stationary on the body while the first conductor is moved. The second conductor has a rounded tip that is electrically conductive, the method further comprising moving the second conductor along the same direction as the first conductor or in a different direction as the first conductor is moved while maintaining the firm pressure on the second conductor. The firm pressure is in a range between 0.5 lbs/in2 and 150 lbs/in2.

The method can further include repeating the treatment cycle an additional one or more times such that a total elapsed treatment time does not exceed 10 minutes. A total elapsed treatment time does not exceed 8 minutes. A total elapsed treatment time does not exceed 6 minutes, and a duration of the treatment cycle does not exceed 4 minutes.

The method can further include repeating the treatment cycle an additional one or more times until the patient subjectively reports a reduction in the pain or until the objective impedance measurement taken on the treated areas of the patient drops below a threshold. The reduction in pain is at least 50% following the repeating. The reduction in pain is at least 70% following the repeating. The threshold of the objective impedance measurement is 20% of the impedance measurement at a start of the first duration. Responsive to the placing at least the first conductor at the same or the new location, the method can further include moving the first conductor along the body while applying firm pressure thereto.

The placing the first conductor includes placing the first conductor at approximately a 45 degree angle relative to a muscle on the body. Responsive to the placing at least the first conductor at the same or the new location, the method can include moving the first conductor along the body while applying firm pressure thereto, the moving the first conductor includes moving the first conductor around the muscle to treat a muscle trigger point on the body while maintaining the first conductor at approximate the 45 degree angle relative to the body.

The method can be carried out while the human or animal is awake and alert and not under any medication to affect a conscious state of the human or animal, and the human or animal is in a prone or seated position at all times throughout.

According to yet other embodiment of the present disclosure, a patient treatment unit or device is directed to delivering non-invasive pulsed energy to living tissue. The patient treatment unit includes a probe stimulus generator circuit configured to output, as a treatment signal, a sequence of direct current (DC) electrical pulses. The DC electrical pulses are outputted at a controlled pulse frequency of about 20 kiloHertz (kHz) and having a pulse voltage defined by a variable supply voltage of the probe stimulus generator circuit. The patient treatment unit further includes a primary probe having a rounded tip configured to contact a body of a human or animal. The primary probe is electrically coupled to the probe stimulus generator circuit so as to receive the DC electrical pulses. The patient treatment unit further includes a secondary probe configured to contact the body. The secondary probe is electrically coupled to the probe stimulus generator circuit to complete an electrical circuit with the primary probe through the body. The patient treatment unit further includes an intensity adjustment circuit configured to control the variable supply voltage, which includes setting the variable supply voltage to a predefined starting voltage upon activation of the probe stimulus generator circuit. The patient treatment unit includes an electronic timer display configured to display an elapsed time in human-understandable decimal numbers in minute and second format. The elapsed time is starting from each activation of the probe stimulus generator circuit and running until a corresponding deactivation of the probe stimulus generator circuit. An electrical current of the DC electrical pulses is in a range between 0.1 milliAmperes (mA) and 6 mA or 8.9 mA while the primary and secondary probes are contacting the body. An operating output voltage across the primary and secondary probes while conducting the treatment signal does not exceed a maximum operating output voltage in a range of 150 to 165 Volts of DC (VDC) while the primary and secondary probes are contacting the body. As used herein, the terms probe, conductor, and electrode may be used interchangeably.

According to another embodiment of the present disclosure, a method of treating pain in a patient is intended to reduce or eliminate the pain. The method includes applying with firm pressure a first probe and a second probe to living tissue of a patient in an area where pain is indicated. The method further includes causing electrical energy to be delivered through the probes and into the tissue in the form of a treatment signal. The treatment signal includes a pulse train of direct current (DC) pulses having a pulse frequency of about 20 kiloHertz (kHz), a pulse current from 0.1 milliAmperes (mA) to 2.5 mA or 6 mA or 8.9 mA for a defined range of load impedance (taken from a range of human children and adults, for example), and a pulse voltage dependent on a variable supply voltage supplied to the probe stimulus generator circuit. The variable supply voltage provides a maximum pulse voltage of about 165 Volts of DC (VDC. While maintaining the firm pressure on the probes, the method further includes moving the probes along the living tissue of the patient in a direction along which a pain signal traverses a body of the patient. The method further includes picking up the probes and moving the probes to the same or a new location on the patient. The method further includes repeating the moving and picking up steps one or more times until the patient subjectively reports a reduction in the pain or until an objective impedance measurement taken on the treated areas of the patient drops below a threshold. The method further includes tracking an elapsed time of treatment by starting at each activation of the treatment mode and stopping at each corresponding deactivation of the treatment. The method further includes displaying the elapsed time of treatment in a minutes and seconds format.

According to yet another embodiment of the present disclosure, a patient treatment unit includes a probe stimulus generator circuit that, while in active operation, generates a treatment signal. The treatment signal includes a pulse train of direct current (DC) pulses having a pulse frequency of about 20 kiloHertz (kHz), a pulse current from 0.1 milliAmperes (mA) to 2.5 mA or 6 mA or 8.9 mA for a defined range of load impedance, and a pulse voltage dependent on a variable supply voltage supplied to the probe stimulus generator circuit. The variable supply voltage provides a maximum pulse voltage of about 165 Volts of DC (VDC). The patient treatment unit further includes a pair of electrically conducting probes coupled to the probe stimulus generator circuit. The pair of electrically conducting probes are for conducting the treatment signal through a body of a human or animal patient, as the load impedance, via non-invasive contact with skin of the patient. The patient treatment unit further includes a mode control circuit configured to activate and deactivate a treatment mode of the patient treatment unit in response to operator input. The treatment mode is characterized by the active operation of the probe stimulus generator circuit. The patient treatment unit further includes an intensity adjustment circuit configured to control the variable supply voltage to start at a predefined starting voltage for each activation of the treatment mode. The patient treatment unit further includes a visual display unit configured to display an elapsed time of treatment by starting at each activation of the treatment mode and stopping at each corresponding deactivation of the treatment, the elapsed time of treatment being displayed in a minutes and seconds format.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the concepts and aspects of the present disclosure, when taken in connection with the accompanying drawings and the appended claims. Additional aspects of the disclosure will be apparent to those of ordinary skill in the art in view of the detailed description of various embodiments, which is made with reference to the drawings, a brief description of which is provided below.

BRIEF DESCRIPTION OF THE DRAWINGS

The disclosure, and its advantages and drawings, will be better understood from the following description of exemplary embodiments together with reference to the accompanying drawings. These drawings depict only exemplary embodiments, and are therefore not to be considered as limitations on the scope of the various embodiments or claims.

Figure 1:
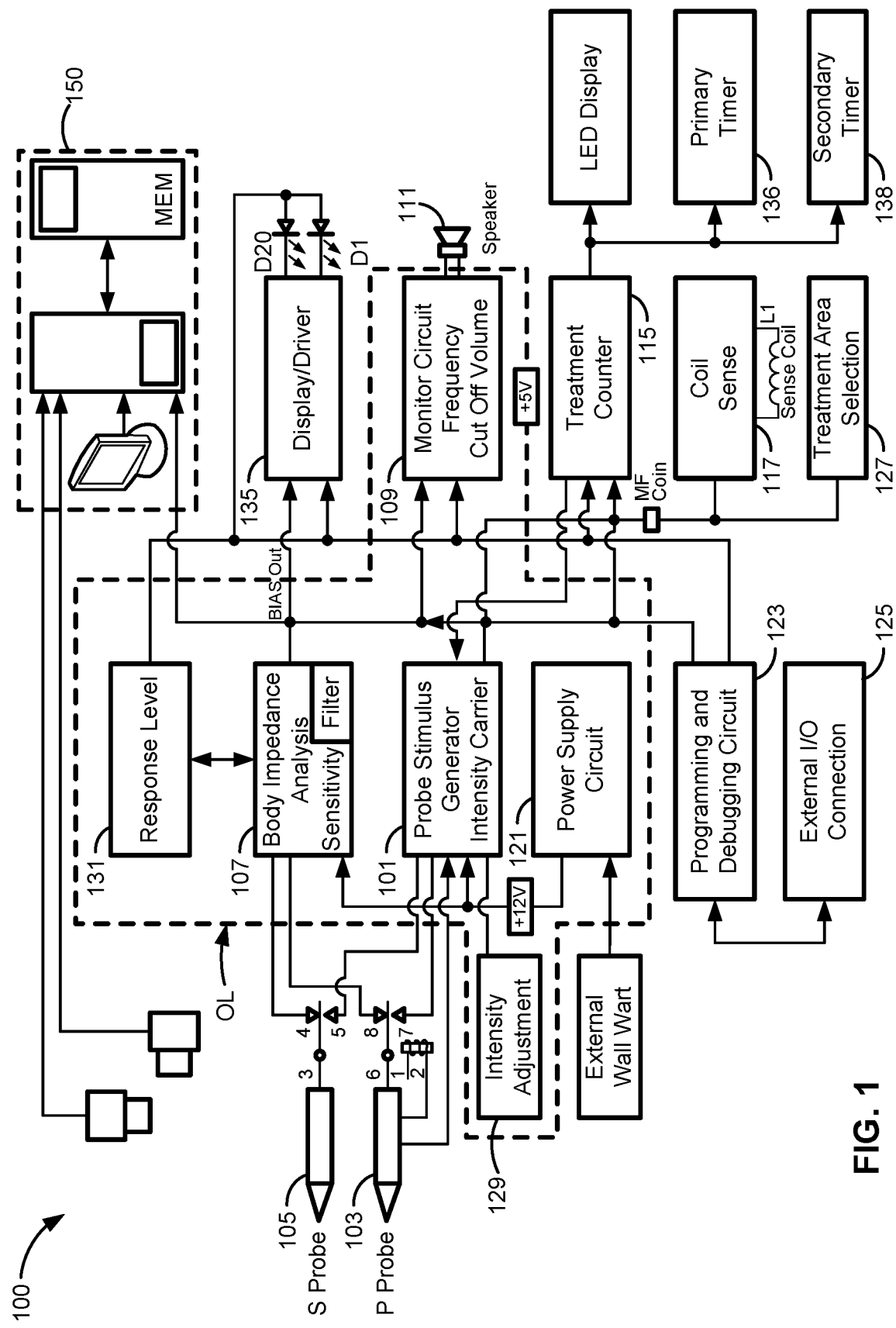
FIG. 1 is a functional block diagram illustrating circuit components of a patient treatment unit, according to an aspect of the present disclosure.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

Various embodiments are described with reference to the attached figures, where like reference numerals are used throughout the figures to designate similar or equivalent elements. The figures are not drawn to scale and are provided merely to illustrate the instant disclosure. Several aspects of the disclosure are described below with reference to example applications for illustration. It should be understood that numerous specific details, relationships, and methods are set forth to provide a full understanding of the disclosure. One having ordinary skill in the relevant art, however, will readily recognize that the disclosure can be practiced without one or more of the specific details, or with other methods. In other instances, well-known structures or operations are not shown in detail to avoid obscuring the disclosure. The various embodiments are not limited by the illustrated ordering of acts or events, as some acts may occur in different orders and/or concurrently with other acts or events. Furthermore, not all illustrated acts or events are required to implement a methodology in accordance with the present disclosure.

Elements and limitations that are disclosed, for example, in the Abstract, Summary, and Detailed Description sections, but not explicitly set forth in the claims, should not be incorporated into the claims, singly, or collectively, by implication, inference, or otherwise. For purposes of the present detailed description, unless specifically disclaimed, the singular includes the plural and vice versa. The word "including" means "including without limitation." Moreover, words of approximation, such as "about," "almost," "substantially," "approximately," "generally," and the like, can be used herein to mean "at," "near," or "nearly at," or "within 3-5% of," or "within acceptable manufacturing tolerances," or any logical combination thereof, for example.

Non-invasive, drug-free treatment and amelioration of pain are endeavors that many have attempted to address through a myriad of therapeutic methods and stimulation means. One area of focus has been the application of electrical energy directly to the skin of a person being treated for a pain condition through metal probe tips that deliver a specific form of energy into the tissue. One early effort to use metal probe tips placed in direct contact with the skin is described in U.S. Pat. No. 8,064,988, which disclosed a very wide range of a billion frequencies ranging from 1 Hertz (Hz) to 1 Gigahertz (GHz), together with flux densities of 0.1 Gauss to 4 Telsa (or 40,000 Gauss), or a range of 400,000 Gauss, and pulse widths spanning 0.34 milliseconds (ms) to 0.74 ms. Only one specific low frequency was disclosed in the range of 1 Hz to 490 Hz. Later, in for example, U.S. Pat. No. 10,085,670, an additional specific frequency range between 4 Kilohertz (kHz) and 20 kHz was disclosed, in addition to the low frequency range of 1-490 Hz. A machine was disclosed with a frequency selector, allowing the operator to switch between low and high frequency ranges and to vary the frequency applied via the probes. While this later patent reduced the ranges of frequencies from a billion, the skilled person still had a range of over 16,500 Hertz to experiment with, not to mention the many other electrical parameters disclosed in these patents (amplitude, pulse width, duty cycle, energy content). Moreover, no quantification of pressure was disclosed in U.S. Pat. No. 8,064,988, nor was there any appreciation that pressure and specific electrical characteristics are particularly efficacious at reducing pain in a very short period of time (e.g., less than 10 minutes). No indication of how much time the energized probes should be placed on the patient, nor any appreciation that the angle that the probes are placed on the body makes any meaningful difference on the reduction in pain. No appreciation was given as to whether movement of one or more probes is efficacious at reducing pain.

Since then, according to this disclosure, it has been discovered, with astonishing results, that at least one specific range of frequency centered around 20 kHz (plus or minus 10%) is particularly effective at reducing, or in many instances, completely eliminating certain types of pain including certain types of chronic pain, together with additional electrical parameters. Moreover, it has also been found that a firm pressure, described below, should be applied on at least one of the energized probes, the angle of the primary probe can be important depending on the area being treated (e.g., joint versus muscle), movement of at least the primary probe can be used to "chase the pain," and there can be a point of diminishing return by over-applying energy to the area being treated for an extended period of time. These and other insights in combination have produced surprising and dramatic reductions in pain and even inflammation, and can also be used in wound treatment to speed up wound healing time as well as to reduce pain around the wound site. Wounds that can be healed using the devices and methods disclosed herein include diabetic wounds, ulcers, infections, cuts, and incision wounds.

The treatment times have been dramatically reduced, and subjective reports indicate that patients feel a substantial reduction in pain after only a single application of probe-delivered electrical energy centered around 20 kHz or in a range of approximately 18-22 kHz, and many report feeling zero pain following one treatment application lasting just a few minutes. Moreover, it has also been discovered in accordance with the present disclosure that certain force pressures, placements, and/or movements of the electrical probes during application of a treatment can also enhance the efficacy of treatment and substantially reduce treatment times. As a result, treatment times have fallen from many minutes to just a few minutes, and within a treatment window lasting just a few minutes or no more than 8 or 10 minutes, the operator of the probes needs to be guided by some visual cue as to when to move a probe or how long a probe has been applying energy at a static location on the skin. Some patients have reported a 100% reduction in pain, or no pain at all despite starting from a 10 out of 10 prior to treatment, within less than 8 minutes of treatment modalities disclosed herein.

A treatment timer circuit is disclosed in U.S. Pat. No. 10,085,670, which displays elapsed time as a hexadecimal number, and was used with an algorithmic evaluation code display 216 to "ensure compliance for both medical outcomes and insurance requirements." At the start of each patient treatment session, the hexadecimal algorithmic evaluation code (AEC) needed to be noted and recorded in the patient's file. This AEC code never reset, and was portrayed as a hexadecimal number instead of decimal numbers and represented a total accumulated treatment time used by the patent treatment unit. The use of hexadecimal numbers (e.g., AE01) made it difficult for the operator to understand how many seconds have elapsed from one treatment to another, and unless the caregiver were familiar with hexadecimal numbers, the AEC counter would not have conveyed any meaningful information to that caregiver. Moreover, because the timer did not reset, the caregiver operator had to jot down or make a mental note of the treatment times from one therapy application to another. This would lead to over-treatments, inconsistent treatment times, confusion by the caregiver operator, and to the operator simply ignoring the AEC codes, resulting in overall sub-optimal treatment efficacy and sometimes over-treatment of an area with diminishing or counterproductive benefit.

It has been determined according to the present disclosure that certain treatment protocols yield particularly effective results and that timing is a key element of such protocols. Timing becomes even more important with the discovery of increased efficacy and concomitant reduction in required treatment durations when using treatment frequencies in the 18 kHz-22 kHz range. In addition, with the discovery that probe application of DC pulses having a frequency centered around 20 kHz is highly effective at treating certain pain conditions, leading to complete pain relief within just a few minutes of a single application of treatment, it has been found to be advantageous to clearly inform the caregiver operator how much treatment time has elapsed of delivery of electrical energy to the patient to ensure that the probes are manipulated on the patient's skin in an optimum manner and for optimum time periods. Moreover, the timer can be used as a training tool to aid novice operators in using the device and manipulating the probes to deliver the most efficacious treatment strategy to a situs of pain or inflammation or a wound. Because the treatment times when using the treatment modalities herein are so short in duration (e.g., 1-4 minutes from the start of the delivery of electrical energy through the body to the cessation of the delivery of electrical energy), the timer showing the elapsed time since the start of the delivery of electrical energy is important to inform the caregiver when the stop delivering energy and/or move one or both probes to a new location.

In addition to the energy characteristics applied to the body, the pressure applied to the body while the energy is being delivered through the electrical conductor is also important in the efficacy of treating pain and reducing the treatment times. A range of firm pressure should be applied to least one of the electrical conductors as the energy is being applied through the conductor contacting the body of the patient being treated.

Conventional TENS electrodes that adhere to the patient's body, apply negligible pressure to the body. A typical TENS electrode weighs approximately 0.0055 lbs, and other than surface tension applied by the adhesive material, there is a negligible amount of pressure applied to the patient's skin while energy is being delivered through the TENS patch. It has been found that pressure should be applied to the conductor while the energy is being applied therethrough. If the pressure is too light, the efficacy of the treatment falls significantly. If the pressure is too hard, the patient can experience discomfort without a concomitant improvement in efficacy. The amount of pressure that can be applied for optimum efficacy also depends on the geometry of the tip of the electrode or conductor contacting the body. Given the range of bodies that the aspects of the present disclosure can be applied to, a minimum pressure expressed as a weight to be applied to the conductor while contacting the body of a person and while delivering the electrical energy disclosed herein is 0.05 lbs (pounds), assuming a hemispherically-shaped or rounded tip on an elongated probe having a diameter of 0.25 inches. A maximum pressure should not exceed 10-15 lbs for the same probe tip. For larger (tip surface area) probe tips, a higher maximum weight or pressure can be tolerated by most patients (e.g., closer to 15 lbs or higher); for smaller (tip surface area) probe tips, a lower maximum weight or pressure can be tolerated (e.g., closer to 10 lbs).

However, for different geometries of the tip of the conductor contacting the body, a higher ceiling of pressure can be applied, such as, for example, 16 lbs depending on the size and weight of the person. The acceptable pressure ranges contemplated herein at the surface of the tip or end of the conductor that makes contact with the body will be expressed herein as pounds per square inch (PSI), assuming a contact surface area corresponding to a round area having a diameter of 0.25 inches.

Using a weight range of 0.05 lbs to 15 lbs, an acceptable range of pressure (expressed as PSI) in one embodiment can be between a minimum of 0.5 lbs/in2 to a maximum of 150 lbs/in2 (or 0.05 lbs to 15 lbs). In other embodiments, the minimum PSI can be any value between 0.6 lbs/in2 and 10 lbs/in2 (or 0.06 lbs to 1 lb). In still other embodiments, the minimum PSI can be any value between 0.6 lbs/in2 and 15 lbs/in2 (or 0.06 lbs to 1.5 lbs). In yet other embodiments, the minimum PSI can be any value between 0.6 lbs/in2 and 20 lbs/in2 (or 0.06 lbs to 2 lbs). In a further other embodiment, the minimum PSI can be any value between 0.6 lbs/in2 and 25 lbs/in2 (or 0.06 lbs to 2.5 lbs). In a still further other embodiment, the minimum PSI can be any value between 0.6 lbs/in2 and 30 lbs/in2 (or 0.06 lbs to 3 lbs). In yet another other embodiment, the minimum PSI can be any value between 0.6 lbs/in2 and 35 lbs/in2 (or 0.06 lbs to 3.5 lbs). In a still further embodiment, the minimum PSI can be any value between 0.6 lbs/in2 and 40 lbs/in2 (or 0.06 lbs to 4 lbs). In another embodiment, the minimum PSI can be any value between 0.6 lbs/in2 and 45 lbs/in2 (or 0.06 lbs to 4.5 lbs). The minimum pressure threshold depends upon one or more of the following: the shape and geometry of the end surface of the conductor contacting the body, the area being treated, the size of the patient being treated, a thickness of the tissue with which the conductor makes contact, the age of the patient. In some embodiments, the maximum PSI can be 100 or 110 or 120 or 130 or 140 lbs/in2. Assuming a primary probe tip diameter of ¼", the maximum weight that should be applied to the tip when pressed against the body is 10 or 11 or 12 or 13 or 14 or 15 pounds. The term "firm pressure" as used herein refers to any operating conductor pressure range within any minimum and maximum quantity disclosed herein, whether expressed as weight (e.g., in pounds, kilograms, or equivalent) or pressure (e.g., pounds or kilograms per square inch or per square centimeter or equivalent), or any other measure by which pressure (compressive force) is quantified. These pressure quantities assume a probe that is positioned relatively orthogonal to the surface of the tissue being treated, although the present disclosure explicitly contemplates that angles between 45-90 degrees can be used depending on the area being treated. Even when the primary probe is held against the body with firm pressure at an angle other than 90 degrees, it is important to maintain a firm pressure on the probe while the tip is contacting the body and energy from the probe is being delivered into the body. In some embodiments, approximately the same firm pressure is applied to both probes 103, 105 when energy is being delivered to the body; in other embodiments, different firm pressure values can be applied to the probes 103, 105. The pressure on the probes determines, in part, a depth that the energy penetrates into the tissue, so the pressure on the probes can be independently adjusted to pinpoint the pain within the tissue.

The present disclosure is also efficacious at wound treatment, so when applying a conductor onto a wound, lighter pressure should be used to avoid discomfort to the patient, but the most pressure a patient can comfortably tolerate without causing further damage or injury to the wound should be applied. For ease of discussion, the range of pressure applied to the body of a patient by an electrical conductor or probe or electrode can be referred to herein as the operating conductor pressure range. Stated differently, a pressure within the operating conductor pressure range is considered to be a firm pressure as used herein. Pressure that falls below the operating conductor pressure range is considered to be light pressure, and pressure above the operating conductor pressure range is considered to be excessive pressure. In all applications herein, firm pressure should be applied to at least one of the conductors through which energy is being delivered to the body of the patient receiving treatment. In one particular application, a weight applied to the conductor tip in the range of 0.1 lbs to 4 lbs, or a pressure between 1 to 40 lbs/in2 (PSI) using a ¼" hemispherical rounded probe tip, is found to be particularly efficacious at treating a wide variety, but not all, of conditions and relatively insensitive treatment locations (e.g., the top of the foot is particularly sensitive and a lighter pressure should be used there so as not to cause discomfort to the patient undergoing treatment). This range of weight pressure is effective for a wide range of treatment applications and locations, but not all.

Generally, one aspect of the present disclosure relates to a treatment unit or device for delivering non-invasive, optimized, and patient-specific pulsed electromagnetic energy while applying pressure within an operating conductor pressure range, which not only eliminates or reduces acute or chronic pain, but further heals the body of a patient. The treatment unit and associated method actually improve the underlying condition that causes pain to emanate in the first place. Rather than simply disrupt the communication of a pain signal, the treatment actually changes the underlying physiology such that a pain inducing condition is remediated. It is believed that in some treatment applications, the combination of pressure within the operating conductor pressure range and the application of pulsed DC energy having a frequency centered around 18-22 kHz optimally reduces pain in the shortest amount of time. These realizations occurred only after conducting many thousands of treatments and soliciting real-time patient feedback using a variety of different electrical energies and pressures over a period of many years. Other realizations include the starting location of the initial position of the electrodes or conductors on the body and how one of those conductors are moved along the body, which depends on the situs of the pain and the type of pain (e.g., tennis elbow versus foot sprain); the amount of time a conductor is held in one position; the angle of one or both conductors relative to the tissue; the total treatment time during a treatment visit (e.g., a treatment visit ends when there is at least a 60 minute period during which no energy is applied to treat the patient, and a new treatment visit starts when at least 60 minutes have elapsed since the last application of energy to the patient under treatment).

Several differences including those mentioned above distinguish the treatment unit and methods of the present disclosure from previous treatments. These differences make the disclosed technology go beyond strictly pain relief into healing the body. For example, one difference is related to broadening the treatment objective from stopping the pain to also healing the underlying condition. The change in treatment objective greatly impacts which body parts are provided with treatment. Instead of simply treating at the source of where the patient perceives pain to be emanating from, the present treatment instead focuses on where the underlying condition is occurring and treat that specific body part. In many cases, the present disclosure requires multiple locations that must be treated. This also has implications as to how long each location must be treated, which requires an integrated timer (that is understandable to a human) into the treatment unit to help the treatment provider give the most efficacious treatment in an efficient manner.

The treatment unit of the present disclosure delivers pulsed electromagnetic energy non-invasively to a patient's involved area. The treatment unit reduces both acute and chronic pain, and with appropriate follow-up treatments can eliminate the pain long term. The current delivered by the treatment unit is defined by a novel set of parameters, which has been thoroughly developed, refined, and researched. Within the treatment unit's configuration are specific characteristics of the electromagnetic current delivery that differentiate the treatment unit from other electric current generating devices, including one or more of the following: (1) a specific frequency of about 20 kHz, (2) a specific DC current in the range of 0.1-2 mA or 0.1-6 mA or 0.1-8.9 mA, (3) a maximum operating output voltage of 165 Volts of direct current (VDC), (4) use of direct vs. alternating current, (5) at least one moveable probe or electrode or conductor as a delivery mechanism of the electrical energy, (6) the angle of the moveable conductor, (7) the pressure applied to the body by the moveable conductor while electrical energy is being provided therethrough, (8) two human-readable timers showing the elapsed time (resettable) when energy is being applied to the body and a lifetime timer (non-resettable) showing how much accumulated time that energy has been delivered by the treatment unit in its lifetime.

The importance of the frequency of the pulsed current (especially direct current) cannot be overstated. At this higher frequency, both current perception thresholds and let-go thresholds are significantly increased. It is possible to employ significantly higher intensities up to 165 Volts (V), as a patient can easily tolerate this high level of intensity in most cases without even feeling any sensation at all. This is the opposite of lower frequency electrical modalities, which can be painful and difficult for a patient to tolerate, limiting the intensity that can be utilized. The lack of any discomfort with the disclosed treatment unit's higher frequency allows the treatment provider to use the treatment unit's full intensity of treatment, which in turn enhances efficacy. Full intensity also enables shorter treatment times to be efficacious. And, at the higher frequency, the treatment unit utilizes very quick, short pulses, which keep the volumetric delivery of energy per pulse low, thus enhancing patient safety.

The frequency current of the treatment unit plays a key part in the ability to deliver the current non-invasively, and, yet, penetrate the epidermis to reach deep into a patient's tissue. Skin itself has a very high level of resistance that can make electromagnetic therapy difficult to deliver beyond the skin and deep into the patient. The high impedance of the skin can be attributed to the lipids of the stratum corneum. However, frequency current with sufficient voltage and short pulse lengths can create "pores" within the skin lipid bilayer, creating a transdermal channel into the depths of tissue. For example, the treatment unit's 20 kHz carrier frequency, with a 50 V output, satisfies these criteria. Furthermore, in some instances, the treatment unit's high frequency and short pulse widths allow the body's tissues to act as sort of condensers. This increased capacitance consequently results in the relieving effects of the treatment unit to persist long after the treatment ends.

The 20 kHz frequency capability of the treatment unit is extremely beneficial. In fact, at a current at about 20 kHz (e.g., plus or minus 2 kHz) a complete nerve block is achievable, which is not seen at other frequencies. The 20 kHz±2 kHz frequency, like the one used with the treatment unit, impacts the voltage-controlled gates and the instigation of second messengers, and triggers a myriad of other beneficial biological actions. At the same time, this 20 kHz frequency makes the current virtually undetectable to the patient, and, with short pulses, safely delivers higher voltage levels that can be used by the treatment provides to generate better outcomes than other electromagnetic therapies.

The treatment unit further utilizes a pulsed direct current that delivers a polarity effect unlike the majority of electrical therapeutic devices, which commonly use an alternating current. Direct current has been proven to be especially beneficial for skeletal and neurological conditions, as well as for wound healing. In fact, direct current promotes peripheral nerve regeneration and, in post-surgical patients, it also expedites nerve function recovery that can contribute to a better healing process. While prior art disclosed DC current, it did not appreciate the combination of energy characteristics that are disclosed herein, which offer the most efficacious pain treatment in an astonishingly short amount of time.

When tissues are damaged, as is the case with surgical incisions, an electrical potential is created between the healthy and damages tissues. This, and other evidence, suggests that wound healing may be partly controlled by electrical signals and, hence, that electrical therapy might influence wound healing. Many clinical investigations over the past 25 years have found that electrical stimulation leads to enhanced would healing. Results for many of the investigations indicate that the healing rate is approximately double in the electrically treated patients. A direct current is the common thread through the research of these investigations. The polarity effect between the anode and cathode appears to have particular consequences to the tissue. The low-intensity direct current may reduce the time needed for superficial wound healing 1.5-2.5 times compared to wounds not receiving such treatment. This form of electrical current can encourage hydration, increase the number of growth factor receptors, increase the rate of collagen formation, stimulate the growth of fibroblasts and granulation tissues, and/or reduce the number of mast cells in the injured area.

Alternating current seems to be more common in other electrotherapy products than direct current, which makes the use of direct current in the treatment unit contributory to its uniqueness. And, as previous studies demonstrate, the use of direct current has many positives on the overall therapy, which makes pulsed direct current an important contributor to the effectiveness of the treatment unit and how it works.

Actively-administered probes or electrodes that can be manually manipulated on and along the body make a meaningful difference in the treatment unit, which offers a distinct delivery methodology via the use of the probes with stainless-steel hemispherical-shaped tips. The caregiver ultimately administers treatment using the probes as the delivery mechanism, which allows for a more-concentrated, high-density current to be delivered directly to the affected area, while at the same time applying pressure within the operating conductor pressure range. Studies have shown the importance of current density, finding that the skin's naturally high resistance can undermine electromagnetic therapy unless the density is sufficient and the frequency of the current is high enough to easily pass through the skin.

In contradistinction to the disclosed probes, and despite the importance of current density and the correlation to probes as the delivery mechanism, the large majority of electrotherapeutic treatments utilize large electrode pads, which are adhered to the patient in a stationary manner. The pads themselves can create a less dense, more-diffuse signal due to their large surface area and paper-thin depth, which can make effective penetration of the skin more difficult, diminish the intensity of the current delivered to the involved area and ultimately making meaningful therapy often unobtainable. Furthermore, the mobility or non-stationary nature of the disclosed probes vs. stationary pads allows the caregiver to cover more territory while still using a dense current and to "follow the pain" as described herein. The movement also allows the treatment provider to flush underlying edema or inflammation, which is highly correlated to pain, out of the area. Movement also can diminish the risk of static electrodes in the wrong or sub-optimal location, and, thereby, undermining the treatment.

In an alternative embodiment, small-diameter (high-density) pads are used instead of or in addition to the disclosed probes. For example, in one embodiment the small-diameter pads are approximately the size of the disclosed probe tips. For example, a small-diameter pad can be used with one probe, where the pad can be affixed or adhered to the patient while the probe is moved to treat the pain. The conductor that provides the return energy can be stationary, depending on the treatment application; or both conductors can be moveable, preferably independently of one another.

The disclosed electromagnetic therapy using the treatment unit is emerging as an excellent treatment option for many painful medical conditions in which unwanted or uncoordinated generation of nerve impulses is a major disabling factor. Existing treatment alternatives, including pharmacological and chemical treatments, or surgery, all have serious shortcomings including that they are not consistently successful. The disclosed electromagnetic therapy may be an effective alternative because it can elicit comparable ionic concentrations and cellular changes as traditional pharmacological nerve blocks. The disclosed electromagnetic therapy also offers a high degree of safety and predictability.

As an overview, the treatment unit is an electroceutical treatment that reduces and/or eliminates pain. Its closest frame of reference is an electrical version of a nerve block. The treatment unit is non-invasive, and offers instant patient feedback. Furthermore, the treatment unit can be used as frequently as needed with no known side effects. The treatment unit re-boots the nerves in the involved area to bring back a normal impulse so that it may supply appropriate neural control to the engaged cells. When impulses can be reset, the painful condition can be reduced or eliminated entirely. By targeting nerves that arguably control all body processes, there is a cascade effect of not only encouraging the release of the body's natural opiates but of improving vascular responses, which is likely responsible for the objective and instant improvements in swelling commonly witnesses with treatments via the treatment unit. The treatment unit uses pulsed electromagnetic energy that is delivered to the patient via a direct current through the treatment unit's probe delivery system and at a carrier frequency that is far higher than almost all other common electrical therapies.

Clinical research demonstrates that treatment at high frequency results in improved results, including fewer required treatments. A draft document of the study is titled "A Clinical Study of the MediPhysics Pain Treatment System for the Treatment for Chronic and Acute Pain," by Frank L. Greenway (December 2005). For example, using a low frequency, it took 12 treatments over four weeks (3 treatments per week) to properly treat a patient's pain. Using the low frequency, 41% of the patients achieved a pain reduction of over 70% of their pain over the 12 treatments, 33% of the patients achieved a pain reduction of 20-70%, and 26% of the patients achieved little or no pain relief (less than 20% relief). Using the low frequency, each individual treatment created an average 52% improvement pre vs. post treatment.

In contrast, recent data from a high-frequency study shows that using a high frequency, such as the approximately 20 kHz frequency of the present disclosure, results in most patients requiring three or fewer treatments and on average only 3.6 treatments. Each treatment averaged 72% pain reduction (vs. 52% improvement for low frequency). All patients experienced 78% or better pain reduction over the full course of their treatments (vs. 41% achieving over 70% at low frequency) and 84% of patients achieved total (100%) reduction of their pain. In another study, in which chronic orchialgia was treated, the average number of treatments required was only 3.2 treatments per patient, and those patients averaged 58% reduction of pain in just 3.2 treatments.

Comparing the above results between the low frequency of the clinical research and the high frequency of the high-frequency study, it is clear that a high frequency reduces the number of treatments per patient and greatly improves the efficacy. Although the amount of energy to which a patient is exposed per pulse is actually lower (making the treatment safer and better tolerated), the total amount of energy delivered to the site of pain is actually higher because of the high frequency.

In accordance with the above unique features, the treatment unit sends electrical pulses to the patient's tissues via primary and secondary probes to provide nerve stimulation to relieve the patient's pain. The treatment unit receives impedance measurements from a patient's tissues using the primary and secondary probes. As the electrical pulses are applied, the impedance measurements are monitored, with a drop in impedance being indicative of less resistance. Lower impedance measurements are correlated to lower perceived levels of pain that the patient experiences. The treatment unit receives impedance information from the patient's tissues, including the body's cellular network, and, by monitoring the received impedance information as additional electrical pulses are applied as pain treatment, the system and method of the present treatment unit assesses and treats pain experienced by the patient's tissues and other physical structures. To be clear, inventive aspects of the present disclosure are not focused on a high frequency range as the sole point of novelty; it is the combination of insights disclosed herein gained over thousands of treatments spanning many years and feedback from dozens of patients.

Figure 2A:
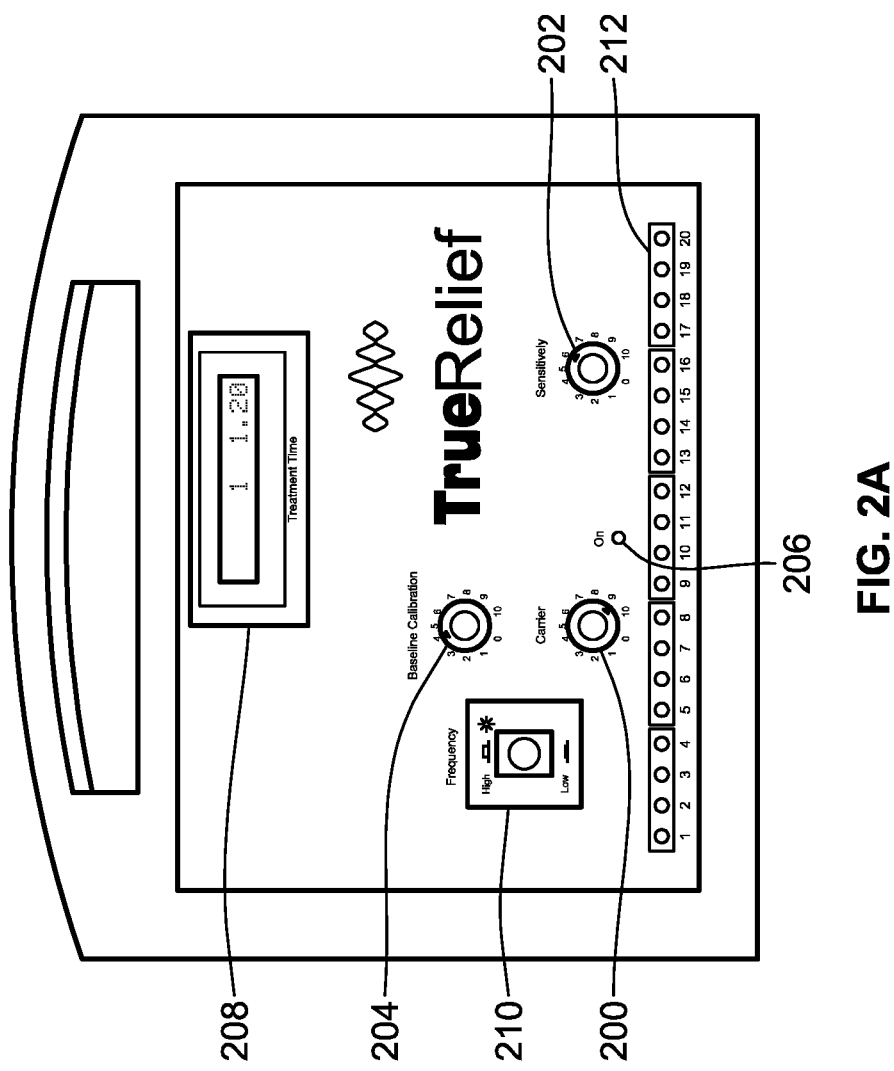
FIG. 2A is a front view illustration of the patient treatment unit of FIG. 1.

In assessing and treating the pain, the treatment unit applies electrical pulse trains at the site of pain, at the tissue abnormality, or upon selected nervous system trigger points or motor points. These trigger or motor points may also coincide with acupuncture or pressure points of the body. As the electrical pulse train is transmitted into the tissue, it encounters the inherent impedance signature produced by the tissue or subject matter under study. Impedance information is generated by this initial analysis and measurement and may be used as a baseline measurement to plan and evaluate treatment. Because the impedance measurement is objective, it can serve as an objective indication of a reduction in the pain and can be used to augment or verify the patient's subjective pain assessment. From the start of a pain treatment to the end of a pain treatment session, which can include multiple cycles of energy applied through the conductors, the reduction in impedance can be at least 10% or 20% or 30% or 40% or greater compared to the start of the pain treatment session. In other words, when the impedance drops to 80% or 70% or 60% or lower of its original value when the energy is first applied through the probes, then the treatment can be concluded as being a success and as having reduced the level of pain. These measurements can be used as a check against the patient's subjective reporting of the level of pain. In some aspects, the objective impedance measurement can be used as an indication of insurance fraud, such as when a patient reports a subjective level of pain that is much greater than the objective criteria. Note that an increase in conductivity is the other side of the impedance coin. That is, instead of a reduction in impedance as an indication of efficacy, an increase in conductivity indicates the same improvement. The terms reduction or decrease in resistivity or impedance means the same thing as an increase in conductivity. The conductance level display 212 shown in FIG. 2A is monitored by the caregiver. When the meter shown on the display 212 represents electrical conductivity, the meter will increase or grow as the conductivity improves. When the meter shown on the display 212 represents body impedance, the meter will decrease or shrink as the impedance drops. In either instance, the caregiver can monitor the changes in the meter to determine when to stop applying energy during a particular treatment cycle. As explained herein, if no movement in the meter is observed after, e.g., 3 minutes of application of energy to the body, the caregiver can decide to continue to apply energy during that treatment cycle for a longer duration of time, e.g., another 1 minute, while monitoring for changes in the meter displayed on the display 212. Like the elapsed treatment time display, the conductance level display 212 also serves an important visual aid to the caregiver to understand how much time duration to apply energy through the probes, and the efficaciousness of a particular energy delivery strategy during a particular treatment cycle. A rapid change in the meter displayed on the display 212 can also cause the caregiver to stop applying energy through the body sooner than the caregiver would have expected, allowing the caregiver to focus on other areas on the body, reducing the overall treatment time.

In addition to evaluating and characterizing a patient's degree of pain, the treatment unit provides therapeutic action to alleviate the pain. The treatment unit may further provide neural stimulation to alleviate pain, reduce healing time, and upon suitable repetition of therapy, result in long-term improved pain management of the afflicted area. Pain is reduced or eliminated by means of the electrical pulse train effect on nociceptive afferent neurons, which are sensitive to electrical stimuli as well as noxious stimuli including thermal, mechanical, and chemical stimuli as described above.

Referring to FIG. 1, a functional block diagram illustrates an exemplary embodiment of a treatment unit in the form of a patient treatment unit 100 that includes a probe stimulus generator circuit 101 for outputting, as a treatment signal, a sequence of DC electrical pulses at a controlled pulse frequency of about 20 kHz (plus or minus 10%). The probe stimulus generator circuit 101 outputs the DC electrical pulses at a pulse voltage defined by a variable supply voltage.

The probe stimulus generator circuit 101 further controls a pulse frequency, a pulse width, and a polarity of the electrical pulse train. Additionally, the probe stimulus generator circuit 101 outputs an electrical pulse train that is a clean waveform, largely free of electrical noise by using rigid electrical component tolerances in a carrier waveform generation circuit. For example, the carrier waveform frequency may be set using a carrier adjustment circuit in combination with a capacitor. This RC circuit may be adjusted to produce the desired carrier frequency of the electrical pulse train. The RC circuit values provide a stable waveform, largely free of electrical noise.

The probe stimulus generator circuit 101 may use a number of different electrical pulse train configurations, depending upon the treatment at hand, but in accordance with the unique parameters disclosed above. For example, a number of different waveforms of variable amplitude may be selected, such as a basic square wave with a pulse width of 9 to 20 us or 14 us and a pulse rate of 20,000 pulses per second, with a pulse amplitude of 100 V, may be selected to treat lower back pain. Optionally, filtering of the electrical pulse train eliminates error signals that often manifest as waveform ripples.

The patient treatment unit 100 further includes a primary probe 103 and a secondary probe 105 that are coupled to the probe stimulus generator circuit 101. As illustrated below in FIG. 2B, the primary probe 103 has a rounded tip that is configured to contact a body of a human or animal and an elongated (dielectric) body having a diameter sufficient to be gripped or grasped or held by a human hand. The elongated form factor aids in the manipulating the primary probe 103 on the skin of the human or animal while maintaining a firm pressure thereon during application of the electrical energy through the probes 103, 105. The primary probe 103 is electrically coupled to the probe stimulus generator circuit 101 so as to receive the DC electrical pulses. The secondary probe 105 is also configured to contact the body of the human or animal, and is electrically coupled to the probe stimulus generator circuit 101 to complete an electrical circuit with the primary probe 103 through the body of the human or animal. The secondary probe 105 can be a stationary conductor such as one that is adhered to the body such that only the primary probe 103 is moveable. This configuration would allow a patient, for example, to self-administer treatment via the primary probe 103 while keeping the stationary probe 105 at a fixed location on the body. The primary probe 103 and/or the secondary probe 105 can optionally include therein a pressure sensor, such as a pressure transducer 262 (see FIG. 2B), configured to sense a pressure applied to the end of the probe 103/105. Optionally, the probe stimulus generator circuit 101 can be configured to require a threshold pressure to be detected via the pressure transducer before outputting the DC electrical pulses through the primary probe 103. Likewise, the probe stimulus generator circuit 101 can be configured to cease outputting the DC electrical pulses through the primary probe 103 when the detected pressure by the pressure transducer falls below the threshold. The threshold can be set to any value at the lower range of the operating conductor pressure range, e.g., 0.5 lbs/in2, and the threshold can be adjusted based on the area being treated and the nature of the pain being treated. For example, a lower pressure threshold value can be set when the area being treated is close to or on a bone or a sensitive area, whereas a higher pressure threshold value can be set when the area being treated is a thick tissue, such as a thigh, or an area that is not as sensitive.

An electrical current of the DC electrical pulses is in a range of 0.1-2 mA or 0.1-6 mA or 0.1-8.9 mA while the probes 103, 105 are in contact with the body. An operating output voltage across the probes 103, 105, while conducting the treatment signal, does not exceed a maximum operating output voltage of 165 VDC while the probes 103, 105 are contacting the body.

The treatment unit 100 includes one or more of a body impedance analysis circuit 107, a monitor circuit 109, an audio speaker 111, a mode control circuit 115, an optional sense circuit 117, a power supply circuit 121, an optional programming and debugging circuit 123, an external input/output connection interface 125, an optional treatment area selection circuit 127, an intensity adjustment circuit 129, a display driver 135, a primary timer 136, and a secondary timer 138. The unit is powered by an external wall wart power supply 119 to supply DC power to the power supply circuit 121. In this example as shown by outline OL in FIG. 1, a number of the circuits 121, 107, 101, 121, 129, 109 are physically mounted and manufactured on a single printed circuit board to reduce electrical noise between components and circuits. The printed circuit board may be a multi-layer printed circuit board to further reduce ambient electrical noise and to generate a clean and error-free pulse train. As will be explained below, additional useful data may be provided to the clinician via an interface module 150. The pair of probes 103 and 105 receives the electrical pulse train and apply the pulse train to the patient's body.

The probe stimulus generator circuit 101 also includes internal monitor functions to ensure the safety and performance of patient treatment unit 100. For example, the probe stimulus generator circuit 101 monitors and checks power supply voltage from power supply circuit 121 and optionally the coil sense indication from sense circuit 117 that the probes 103, 105 are properly connected across a proper tissue or patient. Furthermore, the mode control circuit 115 provides a handshake signal indicating a ready condition that must be detected by probe stimulus generator circuit 101 before a pulse train may be applied to a tissue. The probe stimulus generator circuit 101 can optionally include level shifting circuitry that may be used to alter the carrier current as well as to shift the current and voltage limiting circuitry. The probe stimulus generator circuit 101 will not output the sequence of electrical pulses until the power supply handshake, optionally the sense handshake (if present), and the treatment counter handshake signals all indicate that these circuits 121, 117, 115 are in a ready condition.

Referring to FIG. 2A, an exterior casing of the patient treatment unit 100 has a front surface with a number of controls including a carrier knob 200, a sensitivity or calibration knob 202, a baseline calibration knob 204, a power indicator light 206, a treatment time display 208, a frequency button 210, and a conductance level display 212. The carrier knob 200 controls a frequency of a carrier wave, and the sensitivity/calibration knob 202 adjusts the magnitude of a change in conductance level. The baseline calibration knob 204 adjusts the range of the measurement of conductivity of the patient treatment unit 100, and the power indicator light 206 indicates that the patient treatment unit 100 is on when the light 206 glows. The treatment time display 208 provides a means to track the duration of each patient's treatment, and the frequency button 210 sets an output frequency range, e.g., switches between a high and a low frequency. The conductance level display 212 indicates the conductivity between the probes and is used to track progress being made during treatment, with scale runs, for example, from 1-20. The display 212 also indicates the resistivity or impedance by its converse relationship with conductivity. The display 212 can instead be configured to indicate impedance, in which case a reduction in the meter displayed on the 212 represents a reduction in the impedance (and a corresponding reduction in pain or efficaciousness of treatment).

More importantly, the treatment time display 208 includes at least one of two timer displays that show (a) a total elapsed time or total number of treatments conducted using the patient treatment unit 100 via an aggregate treatment timer display and/or (b) a resettable session time via an elapsed treatment timer display. The aggregate treatment timer does not reset, as it keeps track of the machine's total time across all treatment sessions and/or the total number of treatment sessions conducted using the machine. This is important in particular to provide accountability for maintaining accurate records of the total usage of the patient treatment unit 100, and to track and improve treatment efficacy. The elapsed treatment timer display, which measures the time elapsed each time the treatment mode is engaged and then disengaged, which usually represents a portion of the treatment session at a specific location of the body, resets to zero before a new treatment is initiated. The elapsed treatment timer display restarts each time a new treatment is initiated. A manual reset button (not shown) can be provided to manually reset the elapsed treatment timer on demand; or the elapsed treatment timer display can be configured to automatically reset when the probes 103, 105 begin to deliver energy again through the body.

According to one example, the treatment time display 208 is an electronic timer display that is configured to display an elapsed time in decimal numbers in minute and second format. Alternately, the timer can be expressed visually in manner that readily conveys to the operator how much time has elapsed in a time quantity familiar to the operator. For example, a meter graphic or a dial graphic showing elapsed time can be displayed instead of decimal numbers. The timer displays herein are different from the AEC codes described above in that they are understandable by a layperson. While hexadecimal numbers are understandable to persons familiar with computer arts, for example, they are not familiar to the unskilled layperson. It is important for the operator to see in real time as energy is being provided through the probes how much time has elapsed. The elapsed time starts from each activation of the probe stimulus generator circuit 101 and runs until a corresponding deactivation of the probe stimulus generator circuit 101. A treatment visit by a particular patient can be viewed as a treatment duration or session following which at least 60 minutes or more elapse before the next application of energy to the patient's body. The treatment duration can include many applications of energy to the body at the same or different locations, but there is a short period of time between non-application of energy until the next application of energy on the body (e.g., enough time for the operator to move one or both probes to a new location). When more than 60 minutes have elapsed since the last application of energy, the treatment visit is concluded as of the last application of energy on the body. Because the treatment times when using the aspects of present disclosure are so much shorter compared to treatment times when using prior art treatment approaches, having a human-readable timer displaying the amount of time that has elapsed since the application of energy on the body is important to the operator. Over-treatment can be counter-productive and produce a reduction in efficacy or no material improvement in the reduction of pain. A contiguous, uninterrupted delivery of electrical energy through the body via the conductors is referred to herein as a treatment cycle. A treatment session can comprise multiple treatment cycles, such as when the conductors are moved one or more times. A treatment visit for a given patient can include multiple treatment sessions (which in turn can include one or more treatment cycles), but ends when more than 60 minutes has elapsed since the last application of electrical energy through that patient's body.

Figures 2B, 2C:
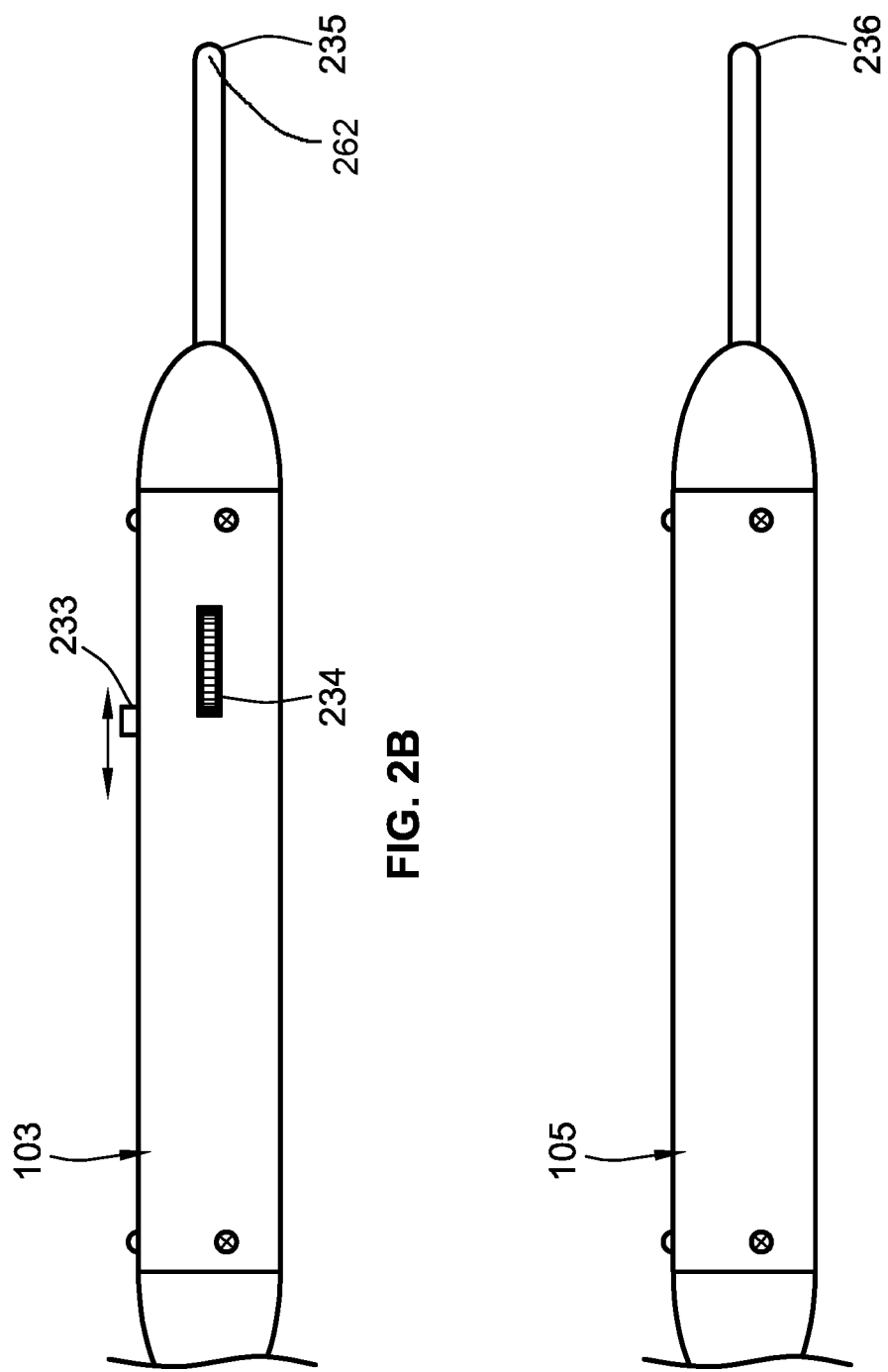
FIG. 2B illustrates a primary probe of the patient treatment unit of FIG. 1, according to one embodiment.
FIG. 2C illustrates a secondary probe of the patient treatment unit of FIG. 1, according to one embodiment.

Referring to FIG. 2B, the primary probe 103 is coupled to the casing of the patient treatment unit 100 with a respective cable and is plugged into a primary probe socket located on a side of the casing. The primary probe 103 has a treatment switch 233 and a probe intensity dial (or wheel) 234, according to one exemplary embodiment. The treatment switch 233 is a binary treatment switch that when pushed towards a probe tip 235 places the patient treatment unit 100 into a treatment mode. Optionally, the probe tip 235 is rounded. Conversely, when the treatment switch 233 is pushed away from the probe tip 235 places the patient treatment unit 100 into a measurement mode. The intensity dial 234 increases a current intensity when dialed (or rotated) toward the probe tip 235, and reduces the current intensity when dialed away from the probe tip 235.

In an alternative exemplary embodiment, which functions consistent with the present disclosure of the patient treatment unit 100, the treatment switch 233 is eliminated entirely, with the probe intensity dial 234 being replaced with a similar-looking dial but one that actually trips into a locked (off) position when dialed all the way away from the probe tip 235. This alternative probe intensity dial effectively performs the functions of both the treatment switch 233 and the above-described probe intensity dial 234. When dialed all the way away from the probe tip 235, the alternative probe intensity dial is positioned into a "locked" off position and the measurement mode is engaged. When the alternative probe intensity dial is dialed toward the probe tip 235 and moved out of its initial "locked" position, the treatment mode is turned on, and, as the alternative probe intensity dial is continued to be dialed toward the probe tip 235, current intensity increases. A benefit of the alternative probe intensity is that it provides a simpler, more efficient manner to switch between the measurement mode and the treatment mode.

In other words, the probe intensity dial 234 is a manual setting for increasing the variable supply voltage to a desired variable treatment voltage. The probe intensity dial 234 is in the form of a detent wheel, according to one exemplary embodiment.

Referring to FIG. 2C, the secondary probe 105 has a respective probe tip 236, but lacks a switch or dial. The secondary probe 105 is coupled to the casing of the patient treatment unit 100 with a respective cable and is plugged into a secondary probe socket located on a side of the casing.

Figure 3A:
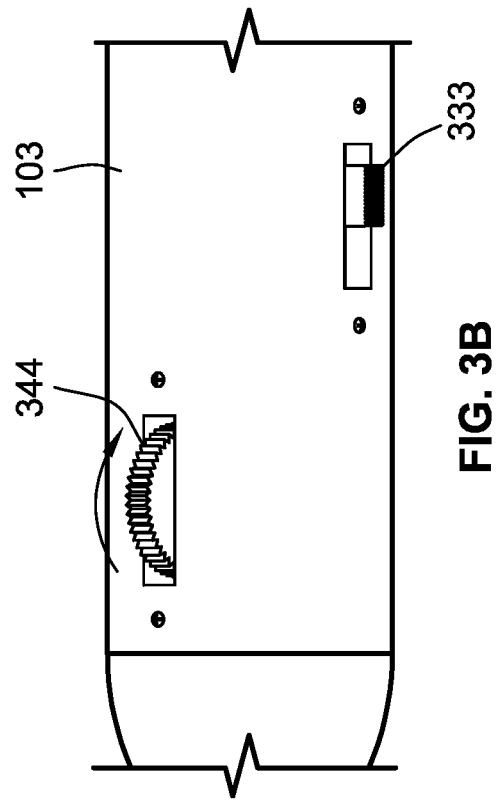
FIG. 3A illustrates a switch of a primary probe, according to another embodiment, in a back position of various treatment positions and intensity levels.
Figure 3B:
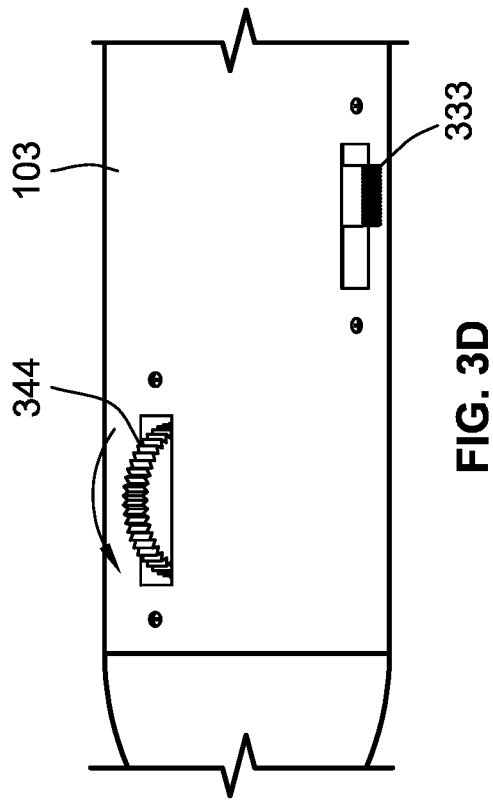
FIG. 3B illustrates a switch of the primary probe of FIG. 3A in the back position with an intensity dial turned towards the back position.

Referring to FIGS. 3A-3D, the primary probe 103 includes a treatment switch 333 that, when in a back position as shown in FIG. 3A, reads the relative conductivity between primary probe 103 and secondary probe 105 in a "measurement" mode. In the measurement mode, a small amplitude current is applied between the probes 103 and 105 to measure the impedance of the tissue to be examined. Voltage and current may be sensed and measured periodically, and impedance readings are calculated periodically. In measurement mode, the treatment switch 333 activates a conductance (or contact) level display 212 in FIG. 2A to provide a visual indication of the conductivity and impedance of the tissue under examination. When pushed forward as shown in FIG. 3B, the treatment switch 333 activates treatment by completing the sense circuit 117 that enables the probe stimulus generator circuit 101 to generate an electrical pulse train output to treat the tissue under examination. When switched to treatment mode, the probe stimulus generator circuit 101 receives a handshake signal from the mode control circuit 115. In this manner, probe stimulus generator circuit 101 provides output voltage to the probes 103 and 105 in the form of the electrical pulse train when the mode control circuit 115 enables the handshake signal.

Figure 3C:
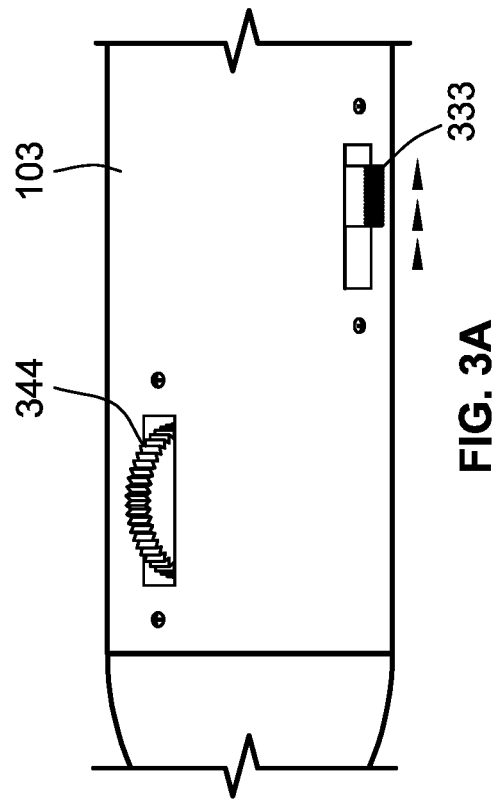
FIG. 3C illustrates a switch of the primary treatment probe of FIG. 3A in the forward position with the intensity dial turned towards the forward position.
Figure 3D:
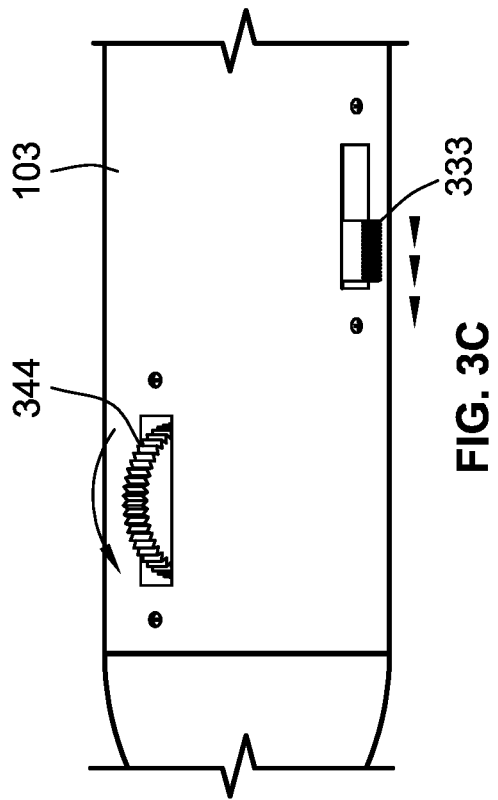
FIG. 3D illustrates a switch of the primary treatment probe of FIG. 3A in the back position with the intensity dial turned towards the forward position.

The probe stimulus generator circuit 101 also checks the power supply circuit 121 to ensure that proper power is provided prior to enabling output current in the form of an electrical pulse train. If the power is not adequate, or if the mode control circuit 115 does not shake hands, the stimulus generator 101 is prevented from outputting the electrical pulse train. The various handshake checks are made by a handshake controller. When the patient treatment unit 100 is in measurement mode, the impedance between the probes (and therefore the impedance of the tissue under examination) is shown in the conductance level display 212 in FIG. 2A. The LED indication in the conductance level display 212 in FIG. 2A remains on during the measurement modes. Additionally, the primary probe 103 includes an intensity dial 344 shown in FIG. 3B that controls the intensity of treatment. At the onset of treatment, the intensity dial 344 is turned toward the back of the probe at its minimum setting as shown in FIG. 3B. The intensity dial 344 is then turned forward toward the front of the probe 103 as shown in FIGS. 3C and 3D until the patient feels the carrier current, but is not uncomfortable.

The mode control circuit 115 detects and tracks an elapsed treatment time indicative of the time the primary probe 103 is delivering the sequence of electrical pulses. The mode control circuit 115 is used to measure and track treatments for regulatory and payment compliance, to ensure patient safety, and for other health or business reasons. A visual indication of the treatment is presented on the primary timer display and on the secondary timer display, in accordance with the applicable disclosure presented above.

Patient compliance with treatment is a medical concern regardless of the form of treatment. Patients must follow through with the prescribed treatments to ensure efficacy and to facilitate recovery. If a patient avoids treatment or takes part in the treatment in a manner not prescribed, the patient's noncompliance masks any effects of the treatment. This leads to great uncertainty as to the effectiveness of the prescribed therapy and whether the current level of treatment is appropriate, or if it is in need of adjustment or discontinuation. Patients are often unwilling to admit they are non-compliant, and when a treatment is difficult or painful, patients may choose to forgo or avoid the treatment despite proven therapeutic benefits. Misuse of the treatment weakens the economic and therapeutic incentives for health care providers and insurance companies to fund or cover the costs of the treatment.

After the treatment switch 333 is activated and treatment begins, the mode control circuit 115 will start the timer which will be visible in the display, and the display will visually track the timed elapsed via minutes and seconds elapsed. The display will continue to count as long as the primary probe 103 remains in treatment mode. Once the treatment switch 333 is deactivated (that is, the patient treatment unit is returned to the measurement mode), the applicable display will stop incrementing but will remain visible. The display will reset to zero and begin to show elapsed time when the treatment switch 333 on primary probe 103 is once again moved forward to re-start additional treatment. At that time, the display will again continue to increment. Instead of minutes and seconds in decimal numbers, the display can display a bar or line graph, circle graphic, hourglass or sand timer graphic, a clock graphic, or similar graphic to indicate how much time in a manner that conveys to a layperson has elapsed since the start of the treatment. The idea here is not to obfuscate or confound the layperson, but to clearly convey to a layperson clinician or caregiver the elapsed time so that the caregiver can track the number of minutes and optionally seconds have elapsed since the start of the application of energy in a treatment mode of the patient treatment unit.

Referring back to FIG. 1, the optional sense circuit 117 is an option that evaluates the presence of a probe connection and enables the probe stimulus generator circuit 101 when the probes 103, 105 are connected to the body impedance analysis circuit 107. The sense circuit 117 ensures that no electrical pulse train is generated when the probes 103, 105 are not properly connected. The wall wart power supply 119 and the power supply circuit 121 provide a stable and regulated 12 volt DC power source to the patient treatment unit 100. The stable and regulated power source helps provide an electrical pulse train free from ambient electrical noise.

The response level circuit 131 measures and indicates the conductivity or impedance between the probes 103 and 105. The intensity adjustment circuit 129 is used to adjust the intensity of the electrical pulses. The intensity of the electrical pulses can be varied or changed by adjusting the current using the intensity dial 344 shown in FIG. 3D.

The intensity adjustment circuit 129 is further configured to control the variable supply voltage, including setting the variable supply voltage to a predefined starting voltage upon activation of the probe stimulus generator circuit 101. The predefined starting voltage is generally a low voltage selected to avoid an initial painful reaction by (or "zapping" of) a patient. After an initial contact occurs between the probes 103, 105 and the body, the predefined starting voltage is changed to a variable treatment voltage as required by each individual, custom application. Thus, after activation of the probe stimulus generator circuit 101, the predefined starting voltage is subsequently increased as treatment proceeds to the treatment voltage, which can vary over the course of the treatment. The increase in current is achieved manually (such as via the probe intensity dial 234) or automatically.

Figure 4:
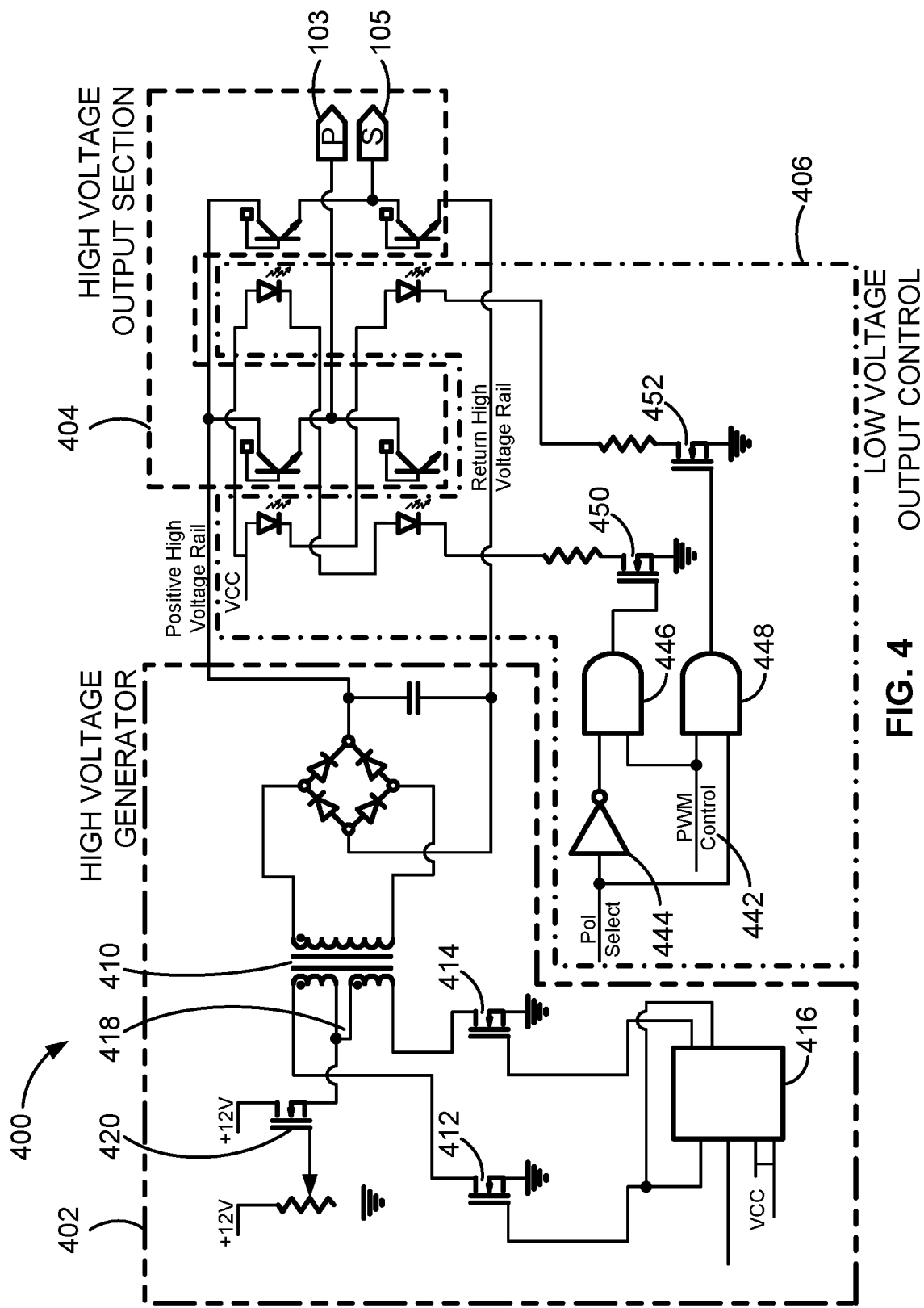
FIG. 4 is a circuit diagram of a waveform generator of the patient treatment unit of FIG. 1.

Referring to FIG. 4, an exemplary pulse forming circuit 400 isolates the high voltage for the probes 103 and 105 that may be included in the probe stimulus generator circuit 101. The pulse forming circuit 400 isolates high voltage from the lower voltage control circuits to produce a cleaner waveform with better pulse shape free of ringing. The resulting unipolar waveform output promotes a unidirectional ionic flow, creating a better net effect. The pulse forming circuit 400 includes a high voltage generator 402, a high voltage output circuit 404 and a low voltage output control circuit 406.

The high voltage generator 402 includes a step up transformer 410, a set of MOSFETs 412 and 414 and a D flip flop 416. A center tap input 418 is coupled to a control MOSFET 420 that is coupled to a DC voltage source such as the power supply circuit 121. A higher clock frequency allows a smaller transformer to be used. The output voltage from the high voltage generator 402 is a function of the center tap voltage coupled to the control MOSFET 420 and the turns ratio of the transformer windings (primary to secondary turns).

The low voltage output control circuit includes an inverter 444, AND gates 446 and 448, and output MOSFETs 450 and 452. The other input of the AND gates 446 and 448 are driven by a pulse width modulation control signal from a control input 442. The pulse width control signal will time how long the output pulse is and at what frequency it is applied. The electrical output specifications are as described above in reference to the parameters of the treatment unit. Additionally, exemplary output waveforms of the patient treatment unit 100 and other optional features are illustrated in U.S. Pat. No. 10,085,670, issued on Oct. 2, 2018, titled "Apparatus And Method For Treatment Of Pain With Body Impedance Analyzer," which is incorporated herein by reference in its entirety.

Figure 5A:
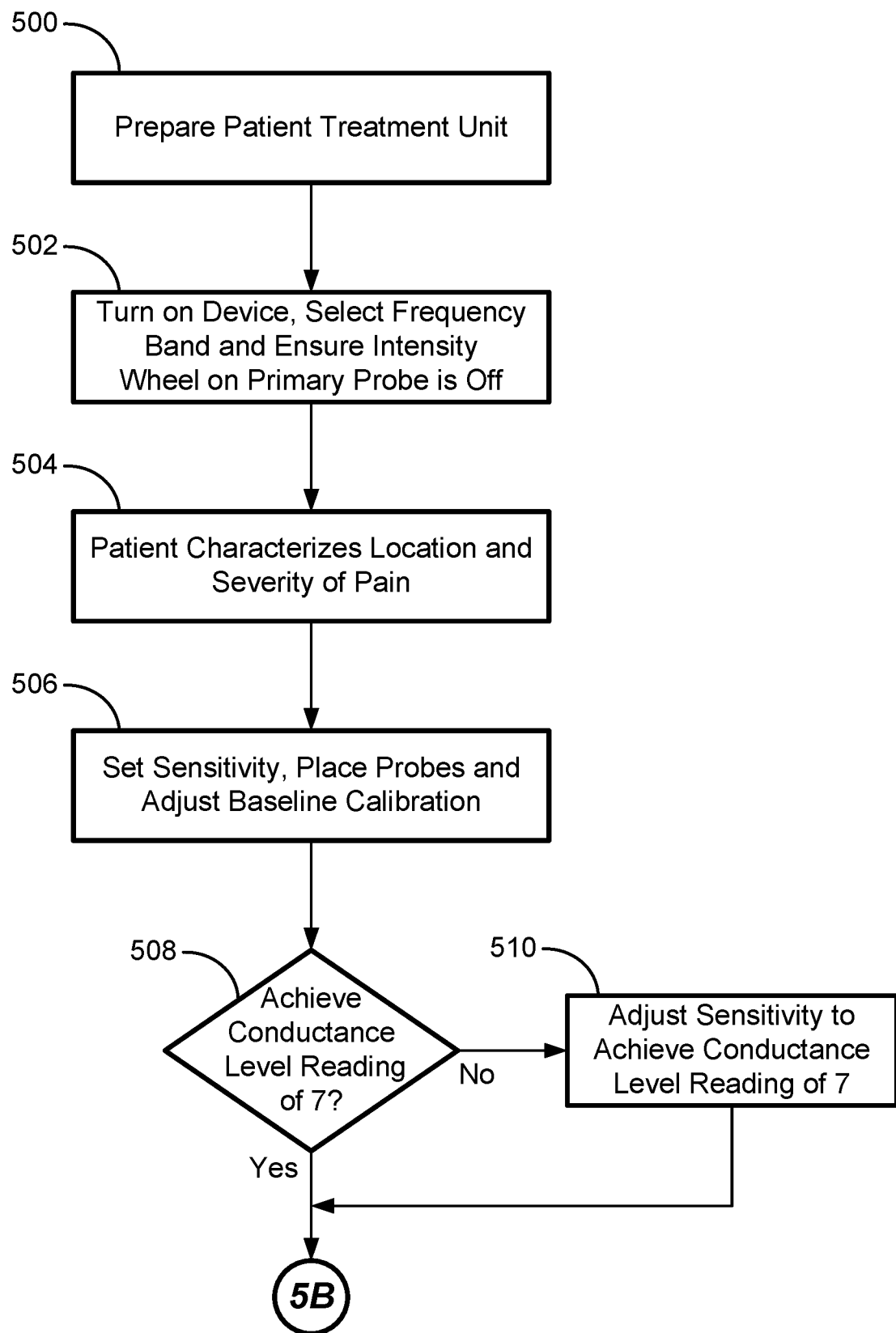
FIG. 5A is a process flow diagram outlining a method of analyzing and treating pain using a patient treatment unit.
Figure 5B:
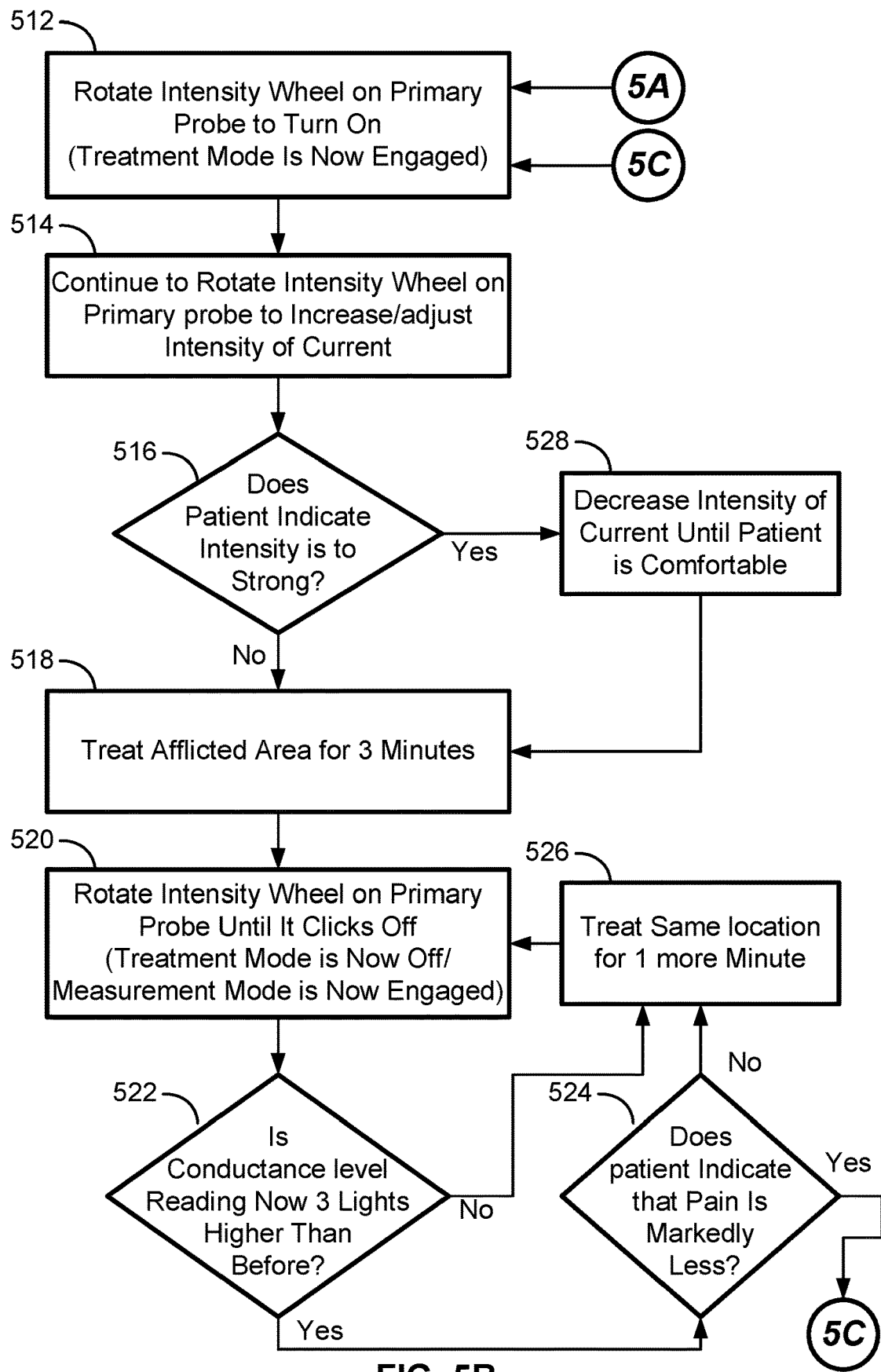
FIG. 5B is a continuation of the process flow diagram of FIG. 5A.
Figure 5C:
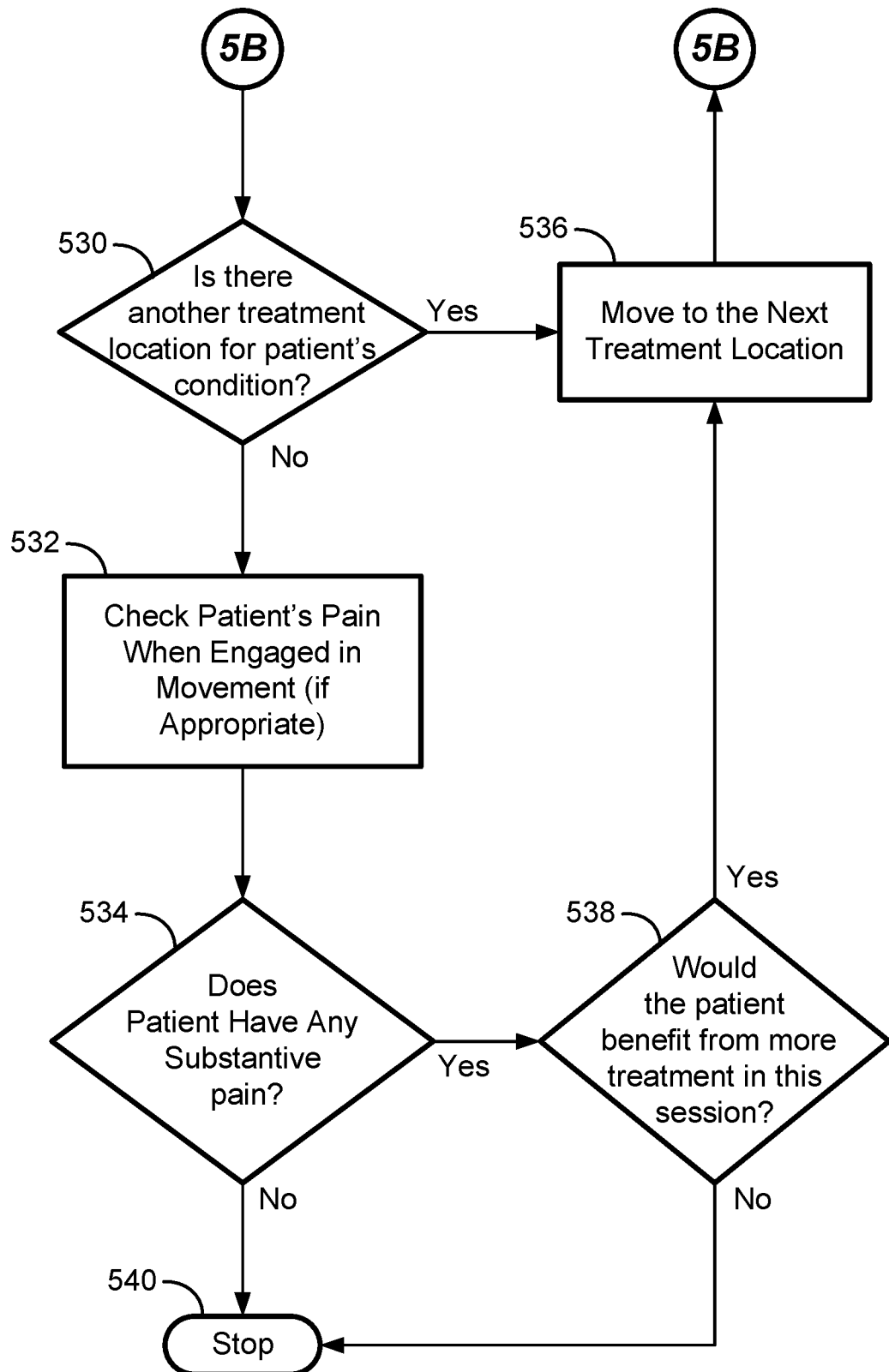
FIG. 5C is a continuation of the process flow diagram of FIG. 5B.

Referring to FIGS. 5A-5C, a method is directed to reducing or eliminating pain using the patient treatment unit 100. As illustrated in FIG. 5A, the patient treatment unit is initially prepared at step 500. The device is turned on at step 502, and a frequency band is selected, ensuring that an intensity wheel on a primary probe is in an off state. A patient characterizes at step 504 the location and severity of the pain. In response to the patient's input, the sensitivity is set at step 506 to an appropriate setting, the probes are placed on a treatment location, and a baseline calibration is adjusted. If a conductance level reading of 7 is not achieved at step 508, then sensitivity is adjusted at step 510 to achieve the conductance level reading of 7.

Referring to FIG. 5B, if the conductance level reading of 7 is achieved, the method proceeds to "1B" by rotating at step 512 an intensity wheel on the primary probe to turn on. This means that the treatment mode is now engaged. At step 514, the method continues to rotate the intensity wheel on the primary probe to increase or otherwise adjust the intensity of electrical current. If the patient indicates at step 516 that the intensity is not too strong, the afflicted area is treated for 3 minutes at step 518. If the patient indicates at step 516 that the intensity is too strong, the intensity of current is decreased at step 528 until the patient is comfortable. The intensity wheel is rotated on the primary probe at step 520 until it clocks off. The treatment mode is now off and the measurement mode is now engaged.

At step 522, if the conductance level reading measured is not 3 lights higher than before, then at step 526 the same location is treated for one more minute at a pressure within the operating conductor pressure range disclosed herein. The intensity wheel on the primary probe is rotated until it clicks off to engage the measurement mode again. If the conductance level reading still shows that it is not 3 lights higher than before, at step 522, the same location is treated again at step 526. At step 522, if the conductance level reading is 3 lights higher than before, a determination is made at step 524 whether the patient indicates that pain is markedly less. If the answer is no, treatment of the same location is again treated for one minute at step 526. If the answer is yes, then the method continues (as illustrated in FIG. 5C) to determine if there is another treatment location for the patient's condition.

Referring to FIG. 5C, a determination is made at step 530 if there is another treatment location for the patient's condition. If the answer is yes, at step 536 the primary and secondary probes are moved to the next treatment location and the method repeats generally the steps illustrated and discussed above in reference to element Z on FIG. 5B. If there is no other treatment location for the patient's condition, at step 532 the patient's pain is checked when engaged in movement (if appropriate). If the patient does not have any substantive pain, at step 540 the treatment is stopped. If the patient does have substantive pain and it is determined that the patient would not benefit from additional treatment, as determined at step 538, the treatment is stopped. If the patient does have substantive pain and it is determined that the patient would benefit from additional treatment, as determined at step 538, the method continues at step 536 with another treatment location and the method repeats generally the steps illustrated and discussed above in reference to element Z on FIG. 5B.

As mentioned above, the treatment modalities disclosed herein can be applied to treat wounds, including chronic wounds such as cuts, punctures, and ulcers, diabetic wounds, non-healing surgical wounds, and puncture wounds. These modalities can be coupled with negative pressure wound therapy (NPWT), compression dressings, and/or topical medications. The methods and treatment devices herein have been used to treat diabetic foot ulcers, pressure ulcers, and venous stasis ulcers. One chronic wound patient who suffered from chronic pain for years was healed within weeks using the treatment modalities disclosed herein after enduring years of non-healing.

Treatment Examples

According to an exemplary treatment, two probes are held and kept about one to two inches apart, depending on the size of the person, and maintained on the body at a pressure within the operating conductor pressure range disclosed herein. The probes are held in-line and next to each other, and are moved up and down sometimes in unison along a specific treated area while keeping the pressure within the operating conductor pressure range. For example, if the treatment is directed to a tendon, the probes are held in-line with the tendon and moved straight up and down in unison following the line of the tendon. The probes are lined-up with edges of the tendon, with the electrical current applied between the edges.

In accordance with a specific tendon example, a tendon that is underneath a kneecap is followed such that same equidistance is maintained for each probe relative to a respective tendon edge as the probes are moved in unison up and down for about three to four minutes, with the probes being in-line with each other. Continuous, slow movement up and down along (not across) fibers of the tendon has shown greater results than side-to-side movement along or across the tendon while maintaining the pressure on the probes within the operating conductor pressure range disclosed herein.

In accordance with another specific tendon example, the Achilles' tendon of the ankle is generally smaller than the patella tendon of the knee. Thus, the two probes cannot be positioned similar to the example discussed above. In the case of the Achilles' tendon the probes are placed in a vertical fashion (e.g., about 90 degrees or orthogonal from the surface of the skin) approximately one to two inches away from each other. They are then moved slowly along the length of the tendon for three to four minutes at a pressure within the operating conductor pressure range disclosed herein. This technique is also effective in treating pain along the peroneus longus tendon (also known as the fibularis longus) and the posterior tibialis tendon. Both of these tendons are quite small and thus the vertical placement of the probes allows for constant contact of the tendon throughout the treatment. In some cases, there may be one area of significant pain along any one of these tendons. This small area can be addressed by holding the secondary probe stationary about an inch away from it and then moving the primary probe superiorly/inferiorly and medially/laterally directly over this small area for about one to two minutes at a pressure within the operating conductor pressure range disclosed herein.

According to another treatment example, a treatment area of a lumbar spine (e.g., L4/L5 or S1/S2) is related to sciatica. The probes are held stationary at the spine at a pressure within the operating conductor pressure range disclosed herein and are moved together in unison down the muscle of the spine into the piriformis muscle. Nerves from the spine are enervated from the same nerve line, rebooting the nerve. Thus, the treatment wakes up the nerve and reboots it through treatment of the muscle.

According to yet another treatment example, the treatment area is an elbow and the treatment is directed to an ulnar nerve entrapment or ulnaritis. A groove is formed in the nerve inside the elbow, with associated numbness to in half of the hand's 3rd digit, the 4th digit, and the 5th digit. The probes are taken and gullied where the ulnar nerve sits. The probes are held in the gully for about one minute at a pressure within the operating conductor pressure range disclosed herein, then run down to the wrist or finger. A similar approach is applied when treating pain associated with carpel tunnel.

Generally, treatment is customized based on the specific part treated. For example, as discussed above, treatment of nerves (which act similar to guitar strings) is different than treatment of muscles (which are pliable and can be more easily felt). When treating nerves, probes are moved over a tunnel and right over nerves while maintaining a pressure on the probes within the operating conductor pressure range disclosed herein. Additionally, treatment of ligaments requires smaller or finer movements of the probes, while treatment of muscles or nerves requires bigger or gross movements. During treatment, the skin turns white and, then, red based on influx of blood circulation. According to one example, the treatment focuses on nickel-sized areas to see where the blood is flowing.

The treatment examples above are in stark contrast to prior treatment methods, which typically place stationary pads for 5-30 minutes at one spot, after which the stationary pads are removed and the treatment is terminated. These pads also do not provide a pressure on the skin within the operating conductor pressure range disclosed herein.

According to another treatment example, an inflammation is treated by moving the probes toward the heart. For example, if treating a knee inflammation, the leg of the patient is elevated and the probes are positioned around the knee joint. The slow, continuous movement of the probes starts below where the inflammation (or swelling) is located. The probes are positioned on either side of the knee joint and are moved up toward the patient's hip (toward the heart). The movement is slow and meticulous around the joint. The distance between the probes is kept at about one to one-and-a-half inches apart.

The angle of attack, or positioning, of the probes relative to the treated body part is relevant and changes based on the type of body part that is being treated. For example, perpendicular positioning of the probes is beneficial when treating joints. By way of specific example, when movement is around a finger, knee, should, or hip, the probes are positioned perpendicular to the respective joints and with really good contact between the probes and the joints. Otherwise, concentration of electrical current is minimized if the probes are angled away from a perpendicular orientation relative to the joint being treated. Similar perpendicularity is beneficial when treatment involves nerves.

When treating muscles, the probes are angled closer to 45 degrees relative to the muscles being treated. The movement of the probes goes around the muscles to capture all angles of the muscle to treat a muscle trigger point.

Pressure applied by the probes while energy is being applied therethrough should be within the operating conductor pressure range disclosed herein, such that skin indentation is generally achieved. The applied pressure should be confidently firm, the patient should feel it, but not be pained by it, keeping in mind the probe tips are small, rounded hemispheres. When reaching a trigger point, more pressure is applied (e.g., at a hip or a piriformis muscle). However, when movement is over a ligament or generally bony area, less pressure is applied to avoid or reduce discomfort.

Typically, the applied current between probes is moved across the problem area (not along the problem). For example, when treating chronic neck or back pain (e.g., stenosis or arthritis) the probes are positioned on either side of the spine and holding the pattern on different levels for one to two minutes. In another example, the probes are moved front to back on shoulders or on hips. In contrast, when treating a knee, the movement is along the side of the knee, treating the front and back of the knee separately.

Treatment results show that nerves, tendons, and muscles show great improvement in physical condition (e.g., reducing pain associating with sciatic tendons). Surprising beneficial results are achieved, for example, in treating sciatica in elderly patients. Other surprising beneficial results are associated with treatment of ankles, which show a great reduction in required treatments, e.g., patients that required 15 treatments with prior methods now require only 3-8 treatments with the treatment unit and methods disclosed herein. Yet other surprising beneficial results are associated with treatment of nerves, tendons, and muscles. Tendon treatment, in particular, provides a "wow" factor result. After treatment of tendons, some patients cancel pre-scheduled surgery. Thus, tendon treatment is extremely effective.

Knowing the anatomy and nuances for that anatomy is helpful in providing the appropriate movements of the probes when treating specific body parts. The movement of the probes, as discussed above, is helpful if performed in a certain way that is beneficial for and is customized to the part being treated. Thus, precise, individual treatment for a particular condition and patient is beneficial when appropriate movement is performed with the independently movable probes. In certain application, a stationary technique may work, individually or in conjunction with the moving technique.

Case Studies on Human Patients

A number of specific patient treatments are described below in which electrical characteristics are the same for each patient. All patients were treated using DC pulsed current at 20,000 Hertz, with full intensity on each patient. All patients were alert, awake, not sedated, and in a seating or prone position during treatments. No other pain alleviating or conscious-state altering therapies such as pain medication were used during any of these non-drug, non-opioid treatments. The probe pressure was within the operating conductor pressure range disclosed herein. The outcomes are great improvements compared to outcomes of previous methods, e.g., (a) more patients received pain relief and (b) more pain relief is achieved by each patient. As a whole, the patients averaged 3.6 treatments each, with each treatment achieving an average of 72% of pain relief for each single treatment. 99% of the patients achieved 70% or better of pain relief over the full course of the treatments. These results are a great improvement when compared to the clinical research described above, in which patients averaged 7.8 treatments each, each treatment achieved an average of 52% pain relief for each single treatment, and 41% achieved 70% or better pain relief over the full course of treatment. Thus, the data below illustrates that the outcomes of the present treatment method is a great improvement over previous treatment methods, with the number of required treatments being reduced in half Additionally, the time required for each treatment has decreased on average by about 30-50%. The letter initials below refer to a distinct, real human patient on which the following treatments were conducted. While many other real human patients were tested, these actual treatments are summarized below as exemplars of different treatment modalities to treat different patient complaints with different resulting therapy improvements and benefits.

LS—This patient had R Achilles tendinitis. Patient LS had seen a doctor and was going to have a surgical debridement of the tendon. For this patient, the probes were held for 4 minutes at the insertion site on the calcaneus while maintaining probe pressure on the skin within the operating conductor pressure range disclosed herein. The probes were then moved superiorly along the tendon, holding the tips perpendicular to the tendon. The proves were slowly moved up the tendon for 2 minutes. Then, the most swollen, tender spot, was located. The secondary probe was held stationary and the primary probe was moved up and down in-line with the tendon at a pressure within the operating conductor pressure range disclosed herein. The primary probe was moved side to side to provide cross friction motion across the tendon. The last spot treated was the tendon insertion into the gastrocnemius. This spot was held this spot for 4 minutes at a pressure within the operating conductor pressure range disclosed herein. This patient had seven treatments. Before treatments began, pain was a 9 on a scale of 0-10 (0 being no pain and 10 being highest level of pain), and when treatments ended pain was zero. 100% pain reduction, which would not have been achievable with prior approaches.

JH—This patient had lateral knee pain making squatting painful. A trigger point was found in the vastus lateralis and the probes were held for 2 minutes at a pressure within the operating conductor pressure range disclosed herein. Then, the probes were placed side to side and slowly worked the probes along the vastus lateralis muscle following the length of the muscle from origin to insertion. This patient had four treatments. Before treatments began, pain was a 5 on a scale of 0-10 (0 being no pain and 10 being highest level of pain), and when treatments ended pain was zero. 100% pain reduction.

MM—This patient had peroneal longus tendinitis and Achilles tendinitis. The treatment was started at the origin of the peroneus longus and the probes were held for 2 minutes at a pressure within the operating conductor pressure range disclosed herein. The probes were then lined-up and moved along the length of the peroneus longus and brevis. The probes were moved slow for 4 minutes at a pressure within the operating conductor pressure range disclosed herein. The primary probe was moved while the secondary probe was kept stationary when the lateral malleolus was reached. This technique was used all the way to the insertion at the 5th metarsal. This patient had two treatments. Before treatments began, pain was a 6 on a scale of 0-10 (0 being no pain and 10 being highest level of pain), and when treatments ended pain was zero. 100% pain reduction.

JOH—This patient had acute onset of shin splints the day before while running. The trigger point was found at the posterior tibialis and the probes were kept on this spot for 2 minutes at a pressure within the operating conductor pressure range disclosed herein. The probes were moved slowly down the length of the posterior tibial tendon to the arch of the foot for a total of 4 minutes at a pressure within the operating conductor pressure range disclosed herein. This patient had two treatments. Before treatments began, pain was an 8 on a scale of 0-10 (0 being no pain and 10 being highest level of pain), and when treatments ended pain was zero. 100% pain reduction.

BM—This was a post-op knee re-alignment patient. He had significant knee pain and swelling. The probe tips were kept perpendicular to the leg, started at the calf, and slowly moved the probes towards the heart, keeping the probes side to side about 1.5 inches apart while maintaining a pressure on the probes within the operating conductor pressure range disclosed herein. This was done for about 4 minutes, working the entire knee. Then, the probes were held at the top of the gastrocnemius muscle and above the knee (posterior) near the medial and lateral femoral condyles. This patient had eleven treatments. Before treatments began, pain was a 9 on a scale of 0-10 (0 being no pain and 10 being highest level of pain), and when treatments ended pain was zero. 100% pain reduction.

MG—This was a patient suffering from R sciatica. The right side of L3/L4/L5/S1 was treated. Then, L4/L5 was traced, moving probes slowly, to the gluteus medius trigger point and held there for 2 minutes at a pressure within the operating conductor pressure range disclosed herein. The probes were then moved back to L4/L5/S1 and, then, slowly moved to piriformis. The probes were held at the piriformis trigger point for 2 minutes, then were slowly moved down to ischial tuberosity. The probes were held there for 2 minutes, then moved for 2 minutes medially and laterally for 2 minutes at a pressure within the operating conductor pressure range disclosed herein. The proves were then moved down the hamstring slowly (2 minutes total) and kept on the trigger point in biceps femoris for 2 minutes at a pressure within the operating conductor pressure range disclosed herein. This patient had six treatments. Before treatments began, pain was an 8 on a scale of 0-10 (0 being no pain and 10 being highest level of pain), and when treatments ended pain was zero. 100% pain reduction.

EB—This patient had thumb pain along the extensor pollicis brevis and abductor pollicis longus tendons. The secondary probe was held still and the primary probe was moved along these tendons for 2 minutes each at a pressure within the operating conductor pressure range disclosed herein. The tendons are too small to run both probes along the tendons. The probes were held stationary for 2 minutes at the CMC joint and at wrist joint at a pressure within the operating conductor pressure range disclosed herein. The patient had only one treatment. Before treatments began, the patient had pain that was a 6 on a scale of 0-10 (0 being no pain and 10 being highest level of pain), and when treatments ended the pain was zero. 100% pain reduction.

OH—This patient was a soccer player with pain along peroneal tendons and calf pain. The trigger points were found at the peroneus longus and brevis. The probes were held there for 2 minutes each at a pressure within the operating conductor pressure range disclosed herein. Then, the probes were lined up along the peroneal tendons and were moved along the entire length around the lateral malleolus to the insertion at the base of the 5th metatarsal. This movement was for a total of 4 minutes. This patient had two treatments. Before treatments began, pain was a 6 on a scale of 0-10 (0 being no pain and 10 being highest level of pain), and when treatments ended pain was zero. 100% pain reduction.

JW—This male patient had R hip flexor strain. This was a college and semi-pro soccer player. The treatment was started at the R ASIS, and were held there for 2 minutes at a pressure within the operating conductor pressure range disclosed herein. The rectus femoris trigger point was found, and the patient's leg was gently extended over the side of the treatment table. Then, the probes were lined-up side to side, and slowly moved down to the knee. This was also performed on the Sartorius muscle and tendon, but here the patient bent his knee and externally rotated his hip. This patient had one treatment. Before treatments began, pain was a 5 on a scale of 0-10 (0 being no pain and 10 being highest level of pain), and when treatments ended pain was zero. 100% pain reduction.

JW—This female patient was a 40 year-old runner that had had pain for 9 months and had been to two chiropractors. She could not run, but was trying to train for a marathon. The patient had pain in left buttocks. The treatment was started at L5 and the probes were held there for 2 minutes at a pressure within the operating conductor pressure range disclosed herein. Then, the probes were moved to S1 for 2 minutes, and then to S2 for 2 minutes. From S2, the probes were moved slowly along the piriformis from the sacrum to the greater trochanter of the femur. The probes were moved slowly for about 4 minutes. The trigger point was found in the piriformis and were kept there for 2 minutes at a pressure within the operating conductor pressure range disclosed herein. This patient had one treatment. Before treatments began, the pain was an 8 on a scale of 0-10 (0 being no pain and 10 being highest level of pain), and when treatments ended pain was zero. 100% pain reduction.

JB—This patient had cervical radiculopathy. The symptoms were that of a C7 radiculopathy. The patient experienced pain back at upper arm and wrist, numbness and tingling in back of arm and middle finger of the right hand. The probes were held at C5/C6/C7/C8 for 2 minutes each. Then, the probes were placed on either side of C6 and C7 for 1 minute each. The probes were moved slowly from C6 down the neck to UT, held for 2 minutes, then to levator scapulae and held for 2 minutes at a pressure within the operating conductor pressure range disclosed herein. The probes were then moved slowly to infraspinatus, down the deltoid, to the triceps, and finally at wrist extensors. This treatment took about 8 minutes. This patient had five treatments. Before treatments began, pain was a 9 on a scale of 0-10 (0 being no pain and 10 being highest level of pain), and when treatments ended pain was zero. 100% pain reduction.

FB—This patient had lumbar radiculopathy with symptoms that were at L4/L5. The probes were held probes at these levels to the right of the spine for 2 minutes, then on either side for 1 minute at a pressure within the operating conductor pressure range disclosed herein. The symptoms were also felt into buttocks and leg. The probes were moved to trace from the spinal segments to the glut medius, then to piriformis, to hamstring, and then peroneals. The treatment took about 10 minutes. Movement was slow while pressure on the probes was maintained within the operating conductor pressure range disclosed herein. This patient had one treatment. Before treatments began, pain was a 10 on a scale of 0-10 (0 being no pain and 10 being highest level of pain), and when treatments ended pain was a 2. 80% pain reduction.

While various embodiments of the present disclosure have been described above, it should be understood that they have been presented by way of example only, and not limitation. Numerous changes to the disclosed embodiments can be made in accordance with the disclosure herein, without departing from the spirit or scope of the disclosure. Thus, the breadth and scope of the present disclosure should not be limited by any of the above described embodiments. Rather, the scope of the disclosure should be defined in accordance with the following claims and their equivalents.

The terminology used herein is for the purpose of describing particular embodiments only, and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

What is claimed is:

1. A patient treatment unit comprising:
a probe stimulus generator circuit that, while in active operation, generates a treatment signal including a pulse train of direct current (DC) pulses having a pulse frequency, a pulse current from 0.1 milliAmperes (mA) to 8.9 mA for a defined range of load impedance, and a pulse voltage dependent on a variable supply voltage supplied to the probe stimulus generator circuit, the variable supply voltage providing a maximum pulse voltage of about 165 Volts of DC (VDC);
a pair of electrically conducting probes coupled to the probe stimulus generator circuit for conducting the treatment signal through a body of a human or animal patient, as the load impedance, via non-invasive contact with skin of the patient, the pair of electrically conducting probes each comprising a rounded hemispherical probe tip;
an adhesive surface configured to attach the rounded hemispherical probe tip of one of the pair of electrically conducting probes to the skin;
a mode control circuit configured to activate and deactivate a treatment mode of the patient treatment unit in response to operator input, wherein the treatment mode is characterized by the active operation of the probe stimulus generator circuit;
an intensity adjustment circuit configured to control the variable supply voltage to start at a predefined starting voltage for each activation of the treatment mode; and
a visual display unit configured to display an elapsed time of treatment by starting at each activation of the treatment mode and stopping at each corresponding deactivation of the treatment, the elapsed time of treatment being displayed in a minutes and seconds format.

2. The patient treatment unit of claim 1, wherein the variable supply voltage changes between a predefined starting voltage and a variable treatment voltage, the predefined starting voltage being lower than the variable treatment voltage.

3. The patient treatment unit of claim 2, further comprising a detent wheel on one of the pair of electrically conducting probes, the detent wheel being rotatable to activate and deactivate the treatment mode.

4. The patient treatment unit of claim 1, wherein the pair of electrically conducting probes include a primary probe having an operating conductor pressure range between 0.5 lbs/in2 and 150 lbs/in2, the primary probe being configured to contact an area of the body of the human or animal patient at an angle between 45-degrees and 90-degrees.

5. A patient treatment unit for delivering non-invasive pulsed energy to living tissue, the patient treatment unit comprising:
a probe stimulus generator circuit configured to output, as a treatment signal, a sequence of direct current (DC) electrical pulses at a controlled pulse frequency and having a pulse voltage defined by a variable supply voltage of the probe stimulus generator circuit;
a primary conductor having an elongated body and a rounded hemispherical tip that is configured to contact a body of a human or animal, the primary conductor being electrically coupled to the probe stimulus generator circuit so as to receive the DC electrical pulses;
a secondary conductor having a rounded hemispherical probe tip and configured to contact the body and electrically coupled to the probe stimulus generator circuit to complete an electrical circuit with the primary conductor through the body;
an intensity adjustment circuit configured to control the variable supply voltage, including setting the variable supply voltage to a predefined starting voltage upon activation of the probe stimulus generator circuit; and
a first electronic timer display configured to display an elapsed time in a human-understandable form, starting from each activation of the probe stimulus generator circuit and running until a corresponding deactivation of the probe stimulus generator circuit;
wherein
at least one of the primary conductor and the secondary conductor includes a probe tip configured to be adhered to the body.

6. The patient treatment unit of 5, further comprising a second electronic timer display configured to display in a human-understandable form a total accumulated time that the probe stimulus generator circuit has delivered the treatment signal since a first time the probe stimulus generator circuit is activated.

7. The patient treatment unit of claim 5, wherein the intensity adjustment circuit is further configured to increase the variable supply voltage from the predefined starting voltage to a variable treatment voltage after the activation of the probe stimulus generator circuit.

8. The patient treatment unit of claim 7, further comprising a primary probe, wherein the primary probe includes the primary conductor and a manual setting for increasing the variable supply voltage to the variable treatment voltage.

9. The patient treatment unit of claim 8, wherein the manual setting is a detent wheel.

10. The patient treatment unit of claim 9, wherein the detent wheel has a locked off position in which a measurement mode is engaged.

11. The patient treatment unit of claim 10, wherein the detent wheel is rotatable towards the rounded tip of the primary probe, away from the locked off position.

12. The patient treatment unit of claim 11, wherein rotation of the detent wheel away from the locked off position results in disengaging the measurement mode and engaging the treatment mode.

13. The patient treatment unit of claim 11, wherein the rotation of the detent wheel away from the locked off position increases the electrical current.

14. The patient treatment unit of claim 9, wherein the detent wheel is the only manual setting on the primary probe.

15. The patient treatment unit of claim 7, wherein the operating output voltage automatically changes between the predefined starting voltage and the variable treatment voltage.

16. The patient treatment unit of claim 5, further comprising an exterior casing in which the probe stimulus generator circuit, the intensity adjustment circuit, and the electronic timer display are enclosed.

17. The patient treatment unit of claim 5, further comprising a pressure sensor in the primary conductor configured to output a pressure applied to the rounded tip, the pressure sensor being configured to measure a pressure at the rounded tip between at least 0.5 lbs/in$^2$ and 150 lbs/in$^2$.

18. The patient treatment unit of claim 5, wherein the pair of electrically conducting probes include a primary probe having an operating conductor pressure range between 0.5 lbs/in2 and 150 lbs/in2, the primary probe being configured to contact an area of the body of the human or animal patient at an angle between 45-degrees and 90-degrees.

19. A method of treating inflammation or a wound in a patient, the method comprising:
- applying a first probe and a second probe to living tissue of a patient in an area where inflammation or a wound is indicated, wherein the first probe is adhered to the tissue of the patient;
- causing electrical energy to be delivered through the probes and into the tissue in the form of a treatment signal, the treatment signal including a pulse train of direct current (DC) pulses having
- a pulse frequency,
- a pulse current from 0.1 milliAmperes (mA) to 8.9 mA for a defined range of load impedance, and
- a pulse voltage dependent on a variable supply voltage supplied to the probe stimulus generator circuit, the variable supply voltage providing a maximum pulse voltage of about 165 Volts of DC (VDC);
- while maintaining the first probe adhered in place, moving the second probe along the living tissue of the patient in a direction along a body of the patient;
- picking up the second probe and moving or applying the second probe to the same or a new location on the patient; and
- repeating the picking up and moving or picking up and applying steps one or more times to treat the inflammation or wound on the patient,
- wherein the first probe and the second probe each comprise a rounded hemispherical probe tip, and the first probe is configured to be adhered to skin of the patient.

20. The method of claim 19, further comprising changing the variable supply voltage from a predefined starting voltage to a variable treatment voltage after initial activation of the treatment signal.

21. The method of claim 19, further comprising manually changing the variable supply voltage between a predefined starting voltage and a variable treatment voltage.

22. The method of claim 19, further comprising automatically changing the variable supply voltage between a predefined starting voltage and a variable treatment voltage.

* * * * *